(12) United States Patent  
Shi

(10) Patent No.: US 12,194,457 B2  
(45) Date of Patent: Jan. 14, 2025

(54) DEVICE AND METHOD FOR COLLECTING PLASMA

(71) Applicant: NowDiagnostics, Inc., Springdale, AR (US)

(72) Inventor: Qinwei Shi, Richmond Hill (CA)

(73) Assignee: NowDiagnostics, Inc., Springdale, AR (US)

( * ) Notice: Subject to any disclaimer, the term of this patent is extended or adjusted under 35 U.S.C. 154(b) by 913 days.

(21) Appl. No.: 16/439,158

(22) Filed: Jun. 12, 2019

(65) Prior Publication Data

US 2019/0374938 A1 Dec. 12, 2019

Related U.S. Application Data

(60) Provisional application No. 62/738,069, filed on Sep. 28, 2018, provisional application No. 62/683,698, filed on Jun. 12, 2018.

(51) Int. Cl.  
  *B01L 3/00* (2006.01)

(52) U.S. Cl.  
  CPC ..... *B01L 3/5023* (2013.01); *B01L 2400/0406* (2013.01); *B01L 2400/0457* (2013.01)

(58) Field of Classification Search  
  CPC .......... B01L 3/5023; B01L 2400/0406; B01L 2400/0457; B01L 9/52; B01L 2200/0621; B01L 2300/0681; B01L 2300/0825; B01L 2300/0864; B01L 2400/086; G01N 1/4005; G01N 33/491  
  See application file for complete search history.

(56) References Cited

U.S. PATENT DOCUMENTS

| | | | |
|---|---|---|---|
| 5,064,541 | A | 11/1991 | Jeng et al. |
| 5,916,521 | A | 6/1999 | Bunce et al. |
| 6,036,659 | A | 3/2000 | Ray et al. |
| 7,238,538 | B2 | 7/2007 | Freitag et al. |
| 7,736,907 | B2 | 6/2010 | Blankenstein et al. |
| 7,785,865 | B2 | 8/2010 | Qinwei |
| 8,105,495 | B2 | 1/2012 | Dorian et al. |
| 8,119,393 | B2 | 2/2012 | Qinwei |

(Continued)

FOREIGN PATENT DOCUMENTS

| | | |
|---|---|---|
| JP | H0696042 B2 | 11/1994 |
| JP | 2002522767 A | 7/2002 |

(Continued)

OTHER PUBLICATIONS

Kim et al. "Simple, Miniaturized Blood Plasma Extraction Method" Anal. Chem. 2013, 85, 11501-11508 (Year: 2013).*

(Continued)

*Primary Examiner* — Dennis White  
(74) *Attorney, Agent, or Firm* — Stanek Lemon Crouse & Meeks, PA

(57) ABSTRACT

Described herein is a device for collecting plasma from a blood sample, the device comprising a body defining a flow channel extending between a proximal and a distal end, the flow channel comprising: a membrane region for supporting a separation membrane that filters red blood cells from the plasma; a plasma collection region for supporting an absorbent membrane that collects the plasma; and a chamber for separating the membrane region from the plasma collection region.

21 Claims, 29 Drawing Sheets

(56) References Cited

U.S. PATENT DOCUMENTS

| | | | |
|---|---|---|---|
| 8,349,618 B2 | 1/2013 | Shi | |
| 8,377,379 B2 | 2/2013 | Feaster et al. | |
| 9,816,979 B2 | 11/2017 | Kelso et al. | |
| 2001/0039059 A1* | 11/2001 | Freitag | G01N 33/558 436/514 |
| 2006/0147349 A1* | 7/2006 | Rhodes | A61B 5/417 422/400 |
| 2008/0076182 A1 | 3/2008 | Takahashi et al. | |
| 2010/0323433 A1* | 12/2010 | Shi | B01L 3/502715 435/287.9 |
| 2011/0189791 A1* | 8/2011 | Shi | B01L 3/5023 422/68.1 |
| 2016/0089669 A1* | 3/2016 | Regnier | B01L 3/5023 422/535 |
| 2017/0318802 A1 | 11/2017 | Hopper | |
| 2018/0074042 A1* | 3/2018 | Kelso | B01L 3/5023 |
| 2020/0166473 A1* | 5/2020 | Hatamian | B01L 9/52 |

FOREIGN PATENT DOCUMENTS

| | | | | |
|---|---|---|---|---|
| JP | 2006502404 A | 1/2006 | | |
| JP | 2008509296 A | 3/2008 | | |
| JP | 2018059756 A | 4/2018 | | |
| WO | WO-2009106331 A2 * | 9/2009 | | B01D 29/014 |
| WO | WO 2009/143601 A1 | 12/2009 | | |
| WO | WO 2013/155617 A1 | 10/2013 | | |
| WO | WO-2016025726 A1 * | 2/2016 | | G01N 33/491 |
| WO | WO 2017/161350 A1 | 9/2017 | | |

OTHER PUBLICATIONS

Leighton Liles "Sample Collection Using Noviplex DUO Plasma Prep Card" Youtube.com, Nov, 7, 2017 https://www.youtube.com/watch?v=ooQCx1DAk08 (Year: 2017).* f Stevenson, R. "Disruptive Sampling Technology: Interview With Tim Schlabach of Novilytic" labcompare.com, Nov. 10, 2017 https://www.labcompare.com/10-Featured-Articles/344087-A-Disruptive-Sampling-Technology-Interview-With-Tim-Schlabach-of-Novilytic/ (Year: 2017).*

Lenk et al. "Capillary Driven and Volume Metred Blood-Plasma Separation" Transducers 2015, Anchorage, Alaska, USA, Jun. 21-25, 2015 (Year: 2015).*

Trum et al. "Novel membrane devices and their potential utility in blood sample collection prior to analysis of dried plasma spots" Bioanalysis (2015) 7(16), 1987-2002 (Year: 2015).*

Notification of Transmittal of the International Search Report and the Written Opinion of the International Searching Authority, or the Declaration, PCT/US19/36763, Aug. 9, 2019, 12 pages.

Notification of Transmittal of the International Search Report and the Written Opinion of the International Searching Authority, or the Declaration, PCT/US19/36763, Jun. 12, 2019, 12 pages.

Notification Concerning Transmittal of International Preliminary Report on Patentability, PCT/US2019/036763, Dec. 15, 2020.

European Search Report, European Application No. 19820080.0, Feb. 8, 2022, 12 pages.

* cited by examiner

DEVICE AND METHOD FOR COLLECTING PLASMA

CROSS-REFERENCE TO RELATED APPLICATIONS

This application claims priority to and the benefit of U.S. Provisional Application Nos. 62/683,698 filed on Jun. 12, 2018 and 62/738,069 filed on Sep. 28, 2018, the disclosures of which are hereby expressly incorporated by reference in their entirety, respectively.

FIELD

The present invention relates to collection of fluid samples. More specifically, the present invention is, in aspects, concerned with fluid collection units and related methods and devices comprising same.

BACKGROUND

Conventional methods for collecting and separating plasma from whole blood usually require the collection of relatively large volumes of blood from a venous blood draw. The whole blood is then separated by centrifugation, resulting in a similarly large volume of plasma and requiring human intervention in the form of a trained technician. Such collection methods require the presence of a patient in a medical setting. Lateral flow devices have been used to filter red blood cells from whole blood, leaving behind plasma. These typically include membranes for filtering the red blood cells from the whole blood and pads in which the plasma is collected. See, for example, U.S. Pat. Nos. 5,064,541; 5,916,521; 7,736,907; 7,785,865; 8,119,393; 8,377,379; and 9,816,979.

U.S. Pat. No. 6,036,659 describes a device for remote-site biological sample collection for laboratory analysis. The device can be made in several configurations which all include separate members for collecting and separating the biological sample into its desired components which are detected or measured.

There is a need for alternative compositions to overcome or mitigate at least some of the deficiencies of the prior art, or to provide a useful alternative.

SUMMARY

In accordance with an aspect, there is provided a device for collecting plasma from a blood sample, the device comprising a body defining a flow channel extending between a proximal and a distal end, the flow channel comprising:
  a membrane region for supporting a separation membrane that filters red blood cells from the plasma; and
  a plasma collection region for supporting an absorbent membrane that collects the plasma;
  wherein flow of the plasma from the separation membrane to the absorbent membrane is impedable.

In an aspect, the flow of the plasma from the separation membrane to the absorbent membrane is blocked.

In an aspect, the flow of the plasma is blocked by removing the separation membrane and/or the absorbent membrane.

In an aspect, the flow of the plasma is blocked by separating the absorbent membrane from the separation membrane.

In an aspect, the separation membrane and the absorbent membrane are contiguous.

In an aspect, the separation membrane and the absorbent membrane are overlapping.

In an aspect, the plasma collection region and the membrane region are removably couplable.

In an aspect, the membrane region and/or the plasma region comprises a tongue that engages with the plasma region and/or the membrane region.

In an aspect, the tongue comprises a protrusion that engages with a corresponding void.

In an aspect, the plasma collection region comprises a top portion and a bottom portion that are removably couplable.

In an aspect, the membrane region comprises a top portion and a bottom portion that are removably couplable.

In an aspect, the top portion of the plasma collection region comprises lateral projections for mating with a top surface of the membrane region.

In an aspect, the top portion of the plasma collection region further comprises grooves on a side surface and/or a bottom surface thereof for mating with a corresponding projection on a top surface of the bottom portion of the plasma collection region.

In an aspect, the bottom portion of the plasma collection region comprises a stand member for inclining the device on a surface.

In an aspect, the top portion of the membrane region comprises arm members for engaging a side surface of the plasma collection region.

In an aspect, the top portion of the membrane region and the bottom portion of the membrane region comprise engagable mated posts and cavities.

In an aspect, top portion of the membrane region further comprises a bottom surface having grooves for mating with a laterally projecting member on a top surface of the bottom portion of the membrane region.

In an aspect, the plasma collection region and the membrane region are removably couplable without an adhesive.

In an aspect, the absorbent membrane is of a predefined volume.

In an aspect, the predefined volume is from about 5 µl to about 50 µl, such as from about 5 µl to about 25 µl, such as from about 10 µl to about 20 µl, such as from about 10 µl to about 15 µl.

In an aspect, the membrane region is enlarged such that a top and bottom wall of the flow channel in the membrane region does not contact the separation membrane.

In an aspect, the membrane region comprises one or more supports that extend from a top and/or bottom wall of the flow channel for supporting the separation membrane.

In an aspect, at least one of the supports extends from the bottom wall of the flow channel.

In an aspect, the device is configured for easy removal of the absorbent membrane.

In an aspect, the device further comprises a handle at the distal end.

In an aspect, the handle comprises an indented circle for supporting a thumb or finger.

In an aspect, the device further comprises a cover.

In an aspect, the device comprises the separation membrane.

In an aspect, the separation membrane has a pore size that accommodates red blood cells without substantial hemolysis.

In an aspect, the separation membrane has an average pore size is greater than about the size of a red blood cell up to about 8 µm, such as from about 6 µm to about 8 µm.

In an aspect, the separation membrane comprises fiberglass.

In an aspect, the separation membrane comprises a colorant that mobilizes with a front of the plasma.

In an aspect, the device further comprises the absorbent membrane.

In an aspect, the absorbent membrane comprises a paper pad.

In an aspect, the absorbent membrane is not adhered to the separation membrane.

In an aspect, the absorbent membrane comprises a colorant that mobilizes with a front of the plasma.

In an aspect, the device allows for collection and flow of the blood from the proximal end through the separation membrane, wherein the red blood cells are retained, and the plasma continues to flow into the absorbent membrane in a single step.

In an aspect, the device does not require the addition of a buffer or diluent to effect flow of the blood through the flow channel.

In an aspect, the device further comprises a window for visually inspecting the sample, for air drying the sample and/or for separating the separation membrane and the absorbent membrane to impede the flow of plasma.

In accordance with an aspect, there is provided a device for collecting plasma from a blood sample, the device comprising a body defining a flow channel extending between a proximal and a distal end, the flow channel comprising:
  a membrane region for supporting a separation membrane that filters red blood cells from the plasma; and
  a plasma collection region for supporting an absorbent membrane that collects the plasma;
  wherein the absorbent membrane is removable from the separation membrane to stop flow of the plasma.

In an aspect, the separation membrane and the absorbent membrane are contiguous.

In an aspect, the separation membrane and the absorbent membrane are overlapping.

In accordance with an aspect, there is provided a device for collecting plasma from a blood sample, the device comprising a body defining a flow channel extending between a proximal and a distal end, the flow channel comprising:
  a membrane region for supporting a separation membrane that filters red blood cells from the plasma; and
  a plasma collection region for supporting an absorbent membrane that collects the plasma;
  wherein the flow of plasma is controllable in a first orientation whereby the separation membrane and the absorbent membrane are in fluid communication and in a second orientation whereby the separation membrane and the absorbent membrane are not in fluid communication.

In an aspect, the fluid communication between the separation membrane to the absorbent membrane is blocked in the second orientation.

In an aspect, the second orientation comprises removing the separation membrane and/or the absorbent membrane.

In an aspect, the second orientation comprises separating the absorbent membrane from the separation membrane.

In an aspect, the separating is permanent.

In an aspect, the separating is temporary.

In an aspect, the separation membrane and the absorbent membrane are contiguous in the first orientation.

In an aspect, the separation membrane and the absorbent membrane are overlapping in the first orientation.

In an aspect, the plasma collection region and the membrane region are removably couplable.

In an aspect, the membrane region and/or the plasma region comprises a tongue that engages with the plasma region and/or the membrane region.

In an aspect, the tongue comprises a protrusion that engages with a corresponding void.

In an aspect, the plasma collection region comprises a top portion and a bottom portion that are removably couplable.

In an aspect, the membrane region comprises a top portion and a bottom portion that are removably couplable.

In an aspect, the top portion of the plasma collection region comprises lateral projections for mating with a top surface of the membrane region.

In an aspect, the top portion of the plasma collection region further comprises grooves on a side surface and/or a bottom surface thereof for mating with a corresponding projection on a top surface of the bottom portion of the plasma collection region.

In an aspect, the bottom portion of the plasma collection region comprises a stand member for inclining the device on a surface.

In an aspect, the top portion of the membrane region comprises arm members for engaging a side surface of the plasma collection region.

In an aspect, the top portion of the membrane region and the bottom portion of the membrane region comprise engagable mated posts and cavities.

In an aspect, top portion of the membrane region further comprises a bottom surface having grooves for mating with a laterally projecting member on a top surface of the bottom portion of the membrane region.

In an aspect, the plasma collection region and the membrane region are removably couplable without an adhesive.

In an aspect, the absorbent membrane is of a predefined volume.

In an aspect, the predefined volume is from about 5 µl to about 50 µl, such as from about 5 µl to about 25 µl, such as from about 10 µl to about 20 µl, such as from about 10 µl to about 15 µl.

In an aspect, the membrane region is enlarged such that a top and bottom wall of the flow channel in the membrane region does not contact the separation membrane.

In an aspect, the membrane region comprises one or more supports that extend from a top and/or bottom wall of the flow channel for supporting the separation membrane.

In an aspect, at least one of the supports extends from the bottom wall of the flow channel.

In an aspect, the device is configured for easy removal of the absorbent membrane.

In an aspect, the device further comprises a handle at the distal end.

In an aspect, the handle comprises an indented circle for supporting a thumb or finger.

In an aspect, the device further comprises a cover.

In an aspect, the device comprises the separation membrane.

In an aspect, the separation membrane has a pore size that accommodates red blood cells without substantial hemolysis.

In an aspect, the separation membrane has an average pore size is greater than about the size of a red blood cell up to about 8 µm, such as from about 6 µm to about 8 µm.

In an aspect, the separation membrane comprises fiberglass.

In an aspect, the separation membrane comprises a colorant that mobilizes with a front of the plasma.

In an aspect, the device comprises the absorbent membrane.

In an aspect, the absorbent membrane comprises a paper pad.

In an aspect, the absorbent membrane is not adhered to the separation membrane.

In an aspect, the absorbent membrane comprises a colorant that mobilizes with a front of the plasma.

In accordance with an aspect, there is provided a device for collecting plasma from a blood sample, the device comprising a body defining a flow channel extending between a proximal and a distal end, the flow channel comprising:

a membrane region for supporting a separation membrane that filters red blood cells from the plasma;

a plasma collection region for supporting an absorbent membrane that collects the plasma; and a chamber for separating the membrane region from the plasma collection region.

In an aspect, a wall of the chamber comprises a proximal vent.

In an aspect, the proximal vent is in a bottom wall of the chamber.

In an aspect, a wall of the chamber comprises a protrusion for breaking surface tension of the plasma in the separation membrane and/or for registering the separation membrane.

In an aspect, the chamber is of a predefined volume.

In an aspect, the predefined volume is from about 5 µl to about 50 µl, such as from about 5 µl to about 25 µl, such as from about 10 µl to about 20 µl, such as from about 10 µl to about 15 µl.

In an aspect, the membrane region is for supporting the separation membrane at a proximal and distal end.

In an aspect, the membrane region is enlarged such that a top and bottom wall of the flow channel in the membrane region does not contact the separation membrane.

In an aspect, the membrane region comprises one or more supports that extend from a top and/or bottom wall of the flow channel for supporting the separation membrane.

In an aspect, at least one of the supports extends from the bottom wall of the flow channel.

In an aspect, the device is configured for easy removal of the absorbent membrane.

In an aspect, the device is formed from two portions that are removably couplable.

In an aspect, the device further comprises a handle at the distal end.

In an aspect, the handle comprises an indented circle for supporting a thumb or finger.

In an aspect, the device further comprises a cover.

In an aspect, the device further comprises a flow path region of predefined volume upstream of the membrane region, wherein the predefined volume is greater than the volume of the chamber.

In an aspect, the device comprises the separation membrane.

In an aspect, the separation membrane comprises a colorant that mobilizes with a front of the plasma.

In an aspect, the separation membrane has a pore size that accommodates red blood cells without substantial hemolysis.

In an aspect, the separation membrane has an average pore size is greater than about the size of a red blood cell up to about 8 µm, such as from about 6 µm to about 8 µm.

In an aspect, the separation membrane comprises fiberglass.

In an aspect, the device comprises the absorbent membrane.

In an aspect, the separation membrane comprises a colorant that mobilizes with a front of the plasma.

In an aspect, the absorbent membrane comprises a paper pad.

In an aspect, the device allows for collection and flow of the blood from the proximal end through the separation membrane, wherein the red blood cells are retained, and the plasma continues to flow into the absorbent membrane in a single step.

In an aspect, the device does not require the addition of a buffer or diluent to effect flow of the blood through the flow channel.

In an aspect, the device further comprises a window for visually inspecting the sample, for air drying the sample and/or for separating the separation membrane and the absorbent membrane to impede the flow of plasma.

In an aspect, the blood sample does not require an anti-coagulant.

In accordance with an aspect, there is provided a one-step method of collecting a plasma sample from a blood sample, the method comprising administering the blood sample to the device described herein comprising the separation membrane and the absorbent membrane, and allowing the sample to be drawn into and through the flow channel.

Other features and advantages of the present invention will become apparent from the following detailed description. It should be understood, however, that the detailed description and the specific examples while indicating aspects of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION

Figure 1:
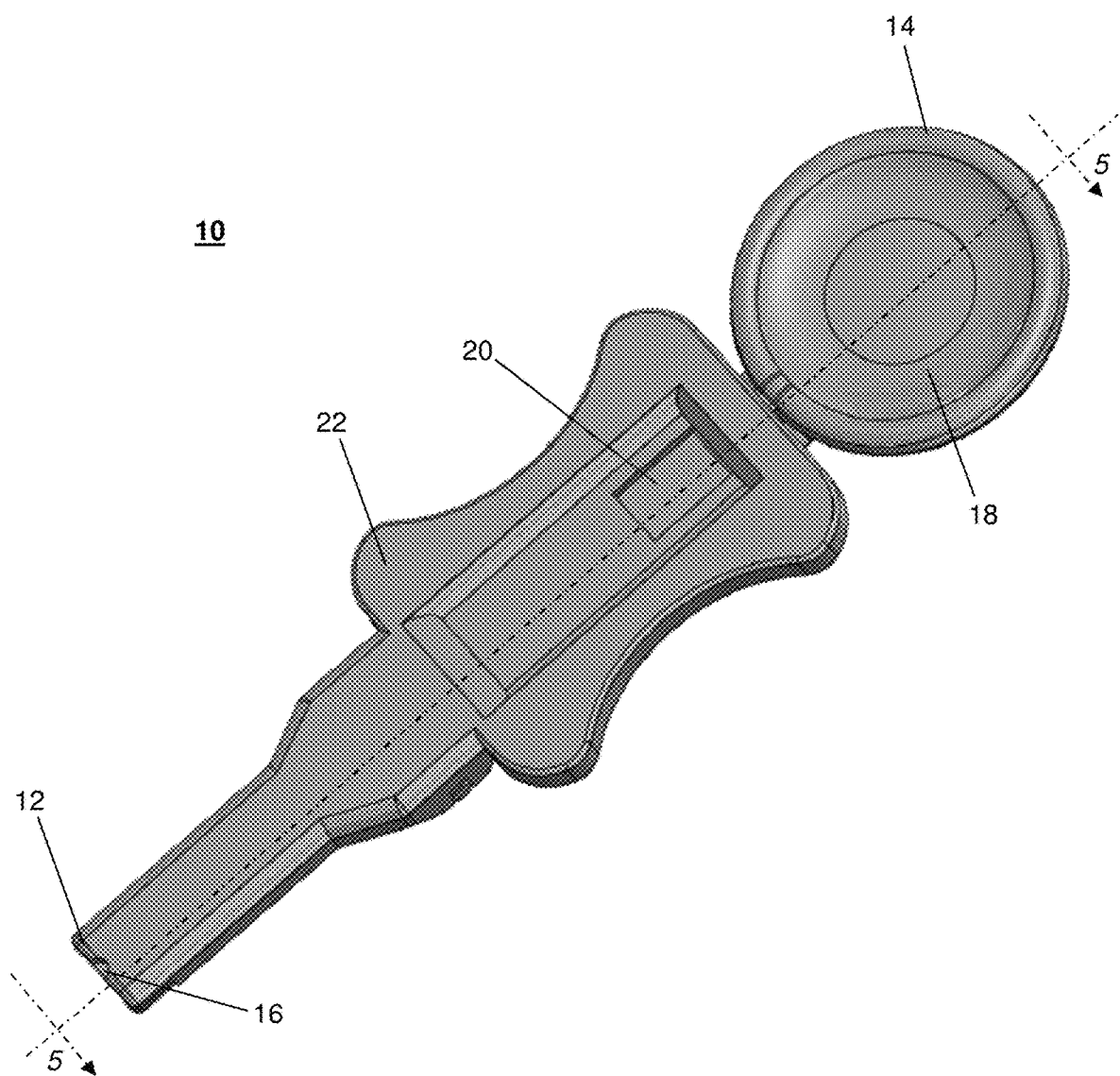
FIG. 1 shows a top perspective view of a first aspect of a device described herein.
Figure 2:
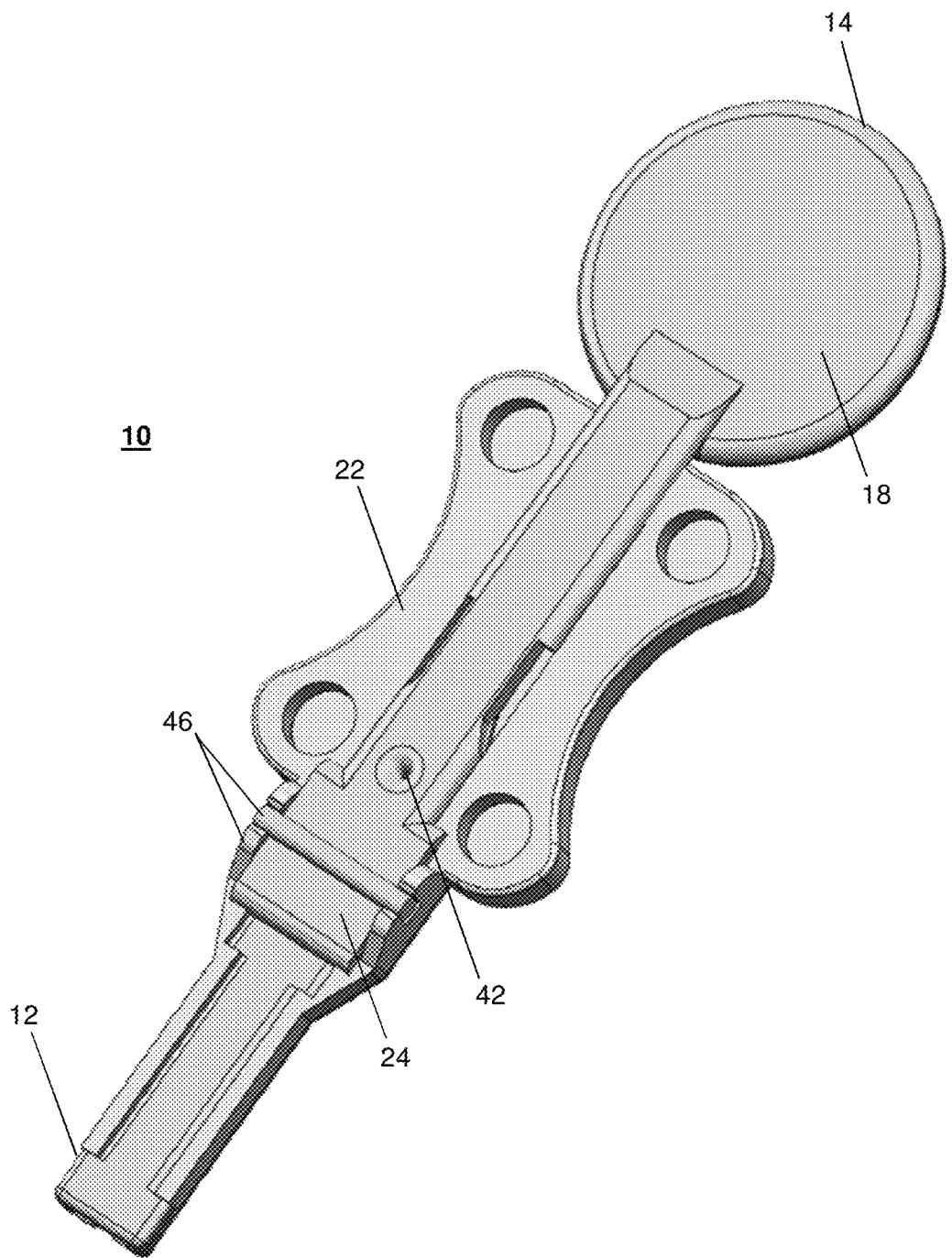
FIG. 2 shows a bottom perspective view of the device of FIG. 1.
Figure 3:
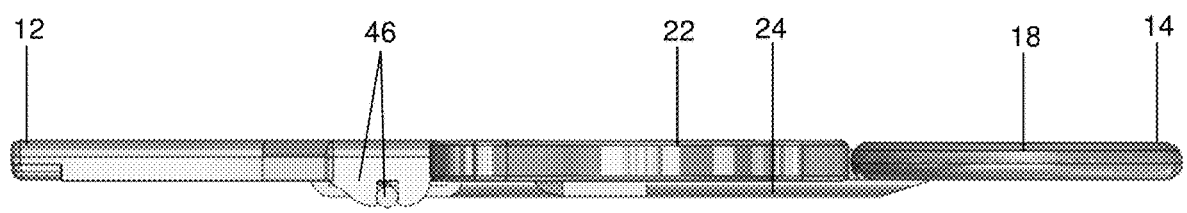
FIG. 3 shows a side plan view of the device of FIG. 1.
Figure 4:
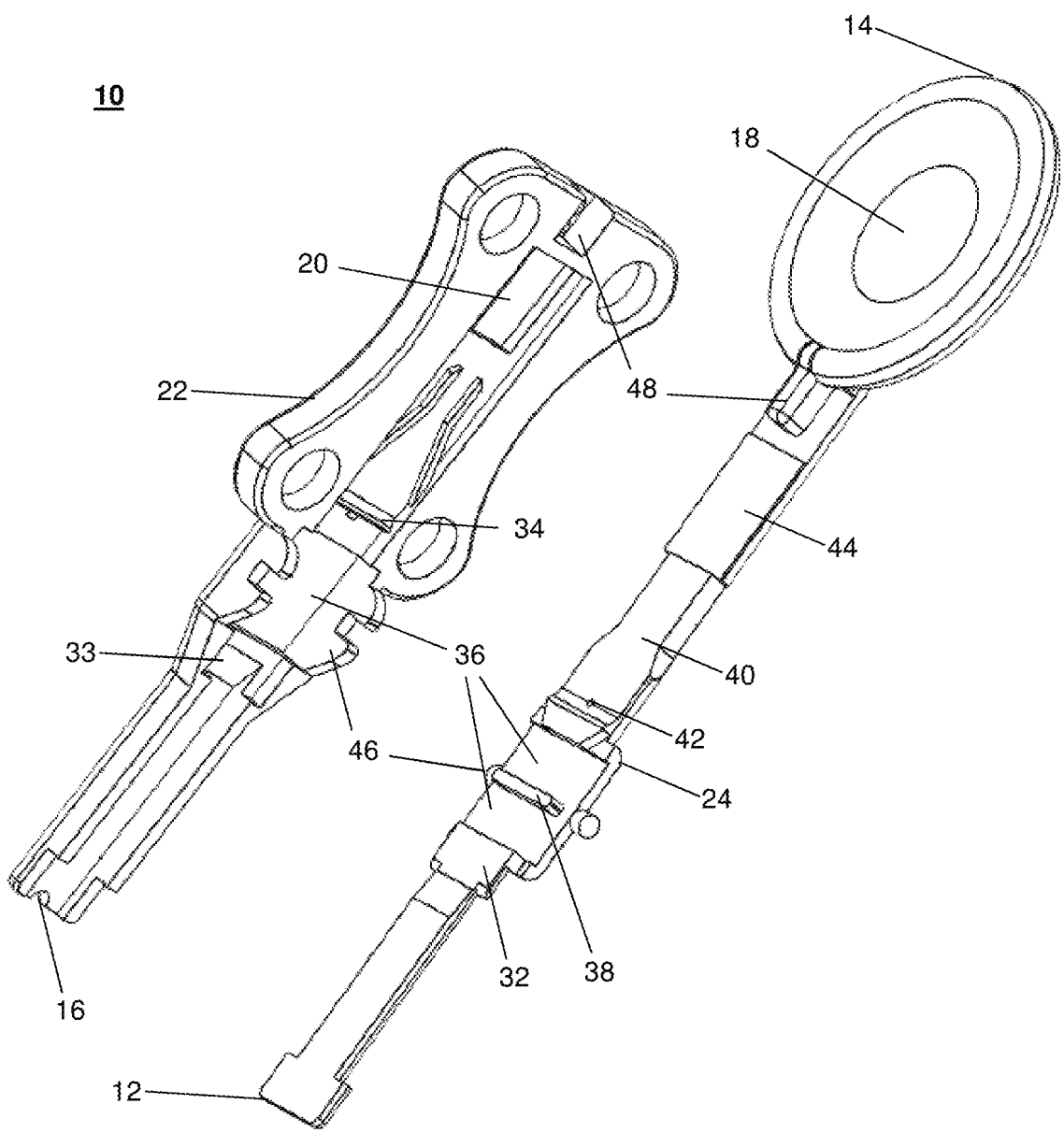
FIG. 4 shows an exploded perspective view of the device of FIG. 1.

Described herein, in aspects, are devices for collecting and separating plasma of a known and predefined volume from a whole blood sample. Through a combination of capillary action and gravity forces, a sufficient yet small volume of plasma will be separated from whole blood and collected in an absorbent membrane retained within the device. The absorbent membrane can be removed from the device and plasma in the membrane can be recovered and assayed directly. Further, the blood cells can be collected separately and also assayed.

In aspects, the flow of the sample through to the absorbent membrane can be impeded so that once the plasma is collected, the separation of the plasma from the sample is permanent. In other words, the user has the option of stopping or disrupting the flow of sample by physically separating the absorbent membrane from the separation membrane, before substantial hemolysis can occur that may obscure or otherwise interfere with the collected plasma. The devices described herein allow for easy separation of plasma from whole blood and, in aspects, quantitation of analytes in plasma and/or the remaining blood cells.

Advantageously, only a small volume of whole blood need be collected for use in the device, such as that which would be obtained from a finger prick. In addition, the blood collected does not need to be transferred to any separate tubing containing an anti-coagulant, nor does the device or any of the separation components described herewith require anti-coagulant. Furthermore, the small resulting volume in the microliter range can be shipped at low cost compared to standard methods, where venous blood is drawn in the milliliter range. Additionally, these tests can be conducted by any person, including the person from whom the blood is being obtained. All that is required is a finger prick blood sample, which is applied to the device and the separating and collection of plasma is carried out automatically by the device with no further input being required by the user.

To this regard, samples can be collected in the home or any other setting by the patient himself for convenience. A self-collected sample can then be sent to a lab for testing. Such self-collection methods are known for capillary blood, where the capillary blood is collected using absorbent paper, which is dried and can be sent to a lab for subsequent testing. However conventional collection methods have at least two limitations: 1) the sample volume is unknown, and therefore analyte concentrations cannot be accurately determined, especially once the sample has dried; and 2) red blood cells may interfere with certain tests, and therefore a plasma sample is preferred. The device described herein is capable of collecting capillary blood, separating the red blood cells from the blood, and automatically isolating a known volume of plasma. The construction of the devices described herein are, in aspects, reversibly connectable allowing for easy assembly and disassembly.

In aspects described herein involving a chamber for separating the membrane region from the plasma collection region, the regions are physically separated, and the membranes do not touch one another. This reduces the risk of the separation being less efficient over time, as once flow of sample stops, hemolyzed blood cannot continue through the empty chamber into the plasma collection region. In aspects described herein that lack a chamber, the separation membrane and the absorbent membrane are in continuous but impedable fluid communication with one another. Once the flow of sample is complete, fluid communication between the membranes can be impeded or disrupted, thereby stopping any flow of sample and eliminating the risk of slow flow of red blood cells or hemolyzed blood cells through the separation membrane and into the absorbent membrane. In other words, the plasma separation in the devices described herein is considered permanent.

Thus, in aspects, the devices described herein can achieve a one-step operation, wherein a small sample of capillary blood is applied to the device and a known volume of plasma is the result. As will be described below, a whole blood sample is applied to the device and, when a sufficient volume is received, the sample enters a plasma separation membrane, such as a fiber glass membrane. In some aspects described herein, as the plasma is separated from the red blood cells, the plasma continues to flow into a chamber with a predefined volume. When the chamber is totally filled, the plasma flows into an absorbent membrane. Due to the presence of an air vent structure, the absorbent membrane will absorb all plasma stored in the second chamber and terminate any further plasma flow to the absorbent membrane. In additional or alternate aspects, the construction of the device permits for the flow of plasma to be impeded once the separation is complete. Thus, once the plasma is collected, the flow can be stopped by, for example, physically separating the membranes from each other. In aspects, the membranes are not physically connected together at any point and are simply touching one another, either edge to edge or slightly overlapped. In this way, the membranes in aspects lack, for example, a backing card that would secure the membranes to one another. They can be simply separated, without the use of any tools, such as scissors, or frangible lines, for example. The used device (or the portion thereof as described herein) can be sent to a lab for testing, typically by removing the absorbent membrane from the device and eluting the plasma in the absorbent membrane for testing such as by mass spectrometry. As the plasma in the membrane is of a predefined and known volume, the resulting tests can be quantitative.

Definitions

The term "proximal" as used herein refers to portions of the device that are closer to the blood collecting end, whereas the term "distal" as used herein refers to portions of the device that are closer to the plasma separating end. The terms "upstream" and "downstream" refer to flow of a fluid from the proximal end (upstream) to the distal end (downstream). The "front" of the fluid refers to the downstream edge of the fluid as it flows from the proximal to the distal end of the device.

The term "analyte" is intended to encompass any chemical or biological substance that is measured quantitatively or qualitatively. In typical aspects, the analyte is one that would be found in a plasma sample. Analytes can include small molecules, proteins, antibodies, DNA, RNA, nucleic acids, carbohydrates, lipids, organic anabolites or metabolites, virus components or intact viruses, bacteria components or intact bacteria, cellular components or intact cells and complexes and derivatives thereof.

For example, the devices described herein find particular use in quickly and easily obtaining plasma samples from subjects without the need for trained healthcare personnel. A simple finger prick blood sample can be obtained and applied to the proximal end of the device, whereby it is drawn into the flow path. When enough sample volume is obtained the sample will flow through the separation membrane, separating red blood cells and other cellular matter and resulting in a plasma sample at the downstream end. By then entering a vented chamber of known volume, a predefined volume of plasma is permitted to enter the absorbent pad. The plasma-containing absorbent pad can then be analyzed by conventional methods to identify and, optionally, quantify, any desired analyte therein. Similarly, the retained cellular matter upstream of the plasma can be analyzed by conventional methods to identify and, optionally, quantify, any desired analyte therein.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," (or vice versa) wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effects described herein.

It will be understood that any component defined herein as being included may be explicitly excluded from the claimed invention by way of proviso or negative limitation, whether implicitly or explicitly defined herein. In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Lateral Flow Device

FIGS. 1 to 7 show a first aspect of a lateral flow device 10 for collecting plasma from a blood sample. FIGS. 8 to 19 show a second aspect of a lateral flow device 100 for collecting plasma from a blood sample.

As shown in FIGS. 1 to 7, the device 10 comprises a proximal end 12 and a distal end 14. At the proximal end 12, a blood sample is applied in a region typically demarcated with a notch 16 or other mark for smooth sample flow from a fingertip. The distal end 14 comprises a handle 18, which is shaped to be easily held by a thumb or finger, for example as a circle with a concave center. The device 10 typically comprises an open window 20, for facilitating plasma drying and observing if the plasma was successfully collected. Optionally, a colorimetric change, such as a line, may occur if the collection is successful.

Figure 5:
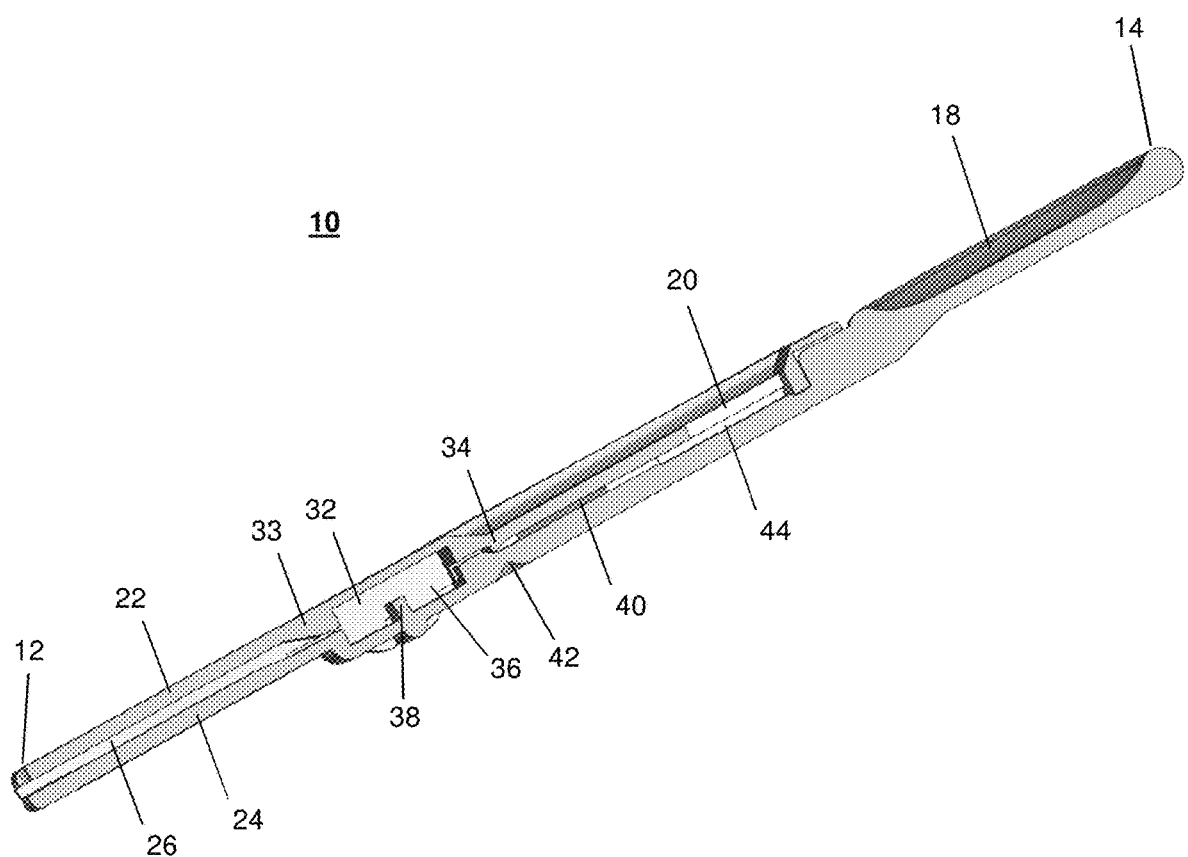
FIG. 5 shows a cross-sectional view along line 5-6 of the device of FIG. 1, without membranes.
Figure 6:
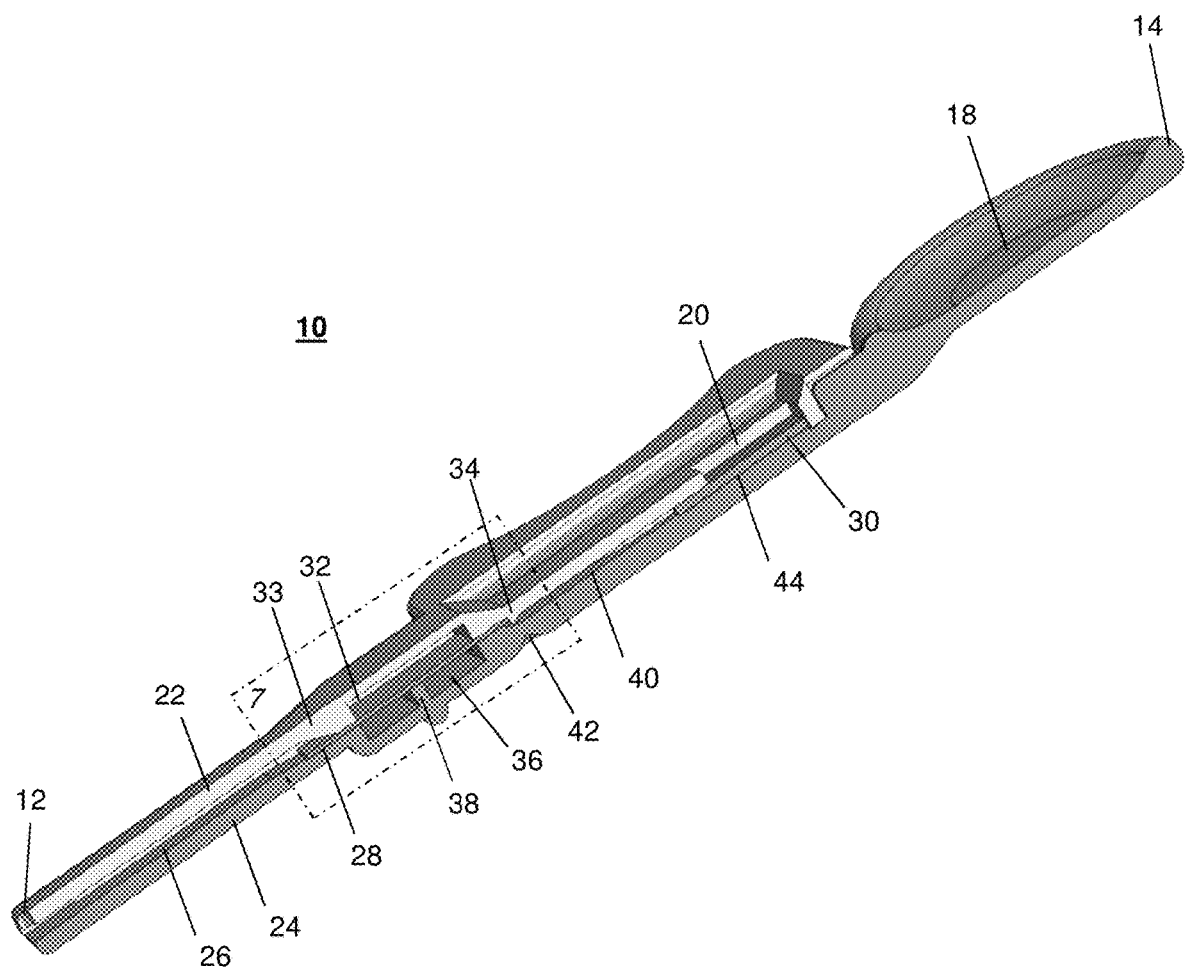
FIG. 6 shows a cross-sectional view along line 5-5 of the device of FIG. 1, with separation and absorbent membranes.
Figure 7:
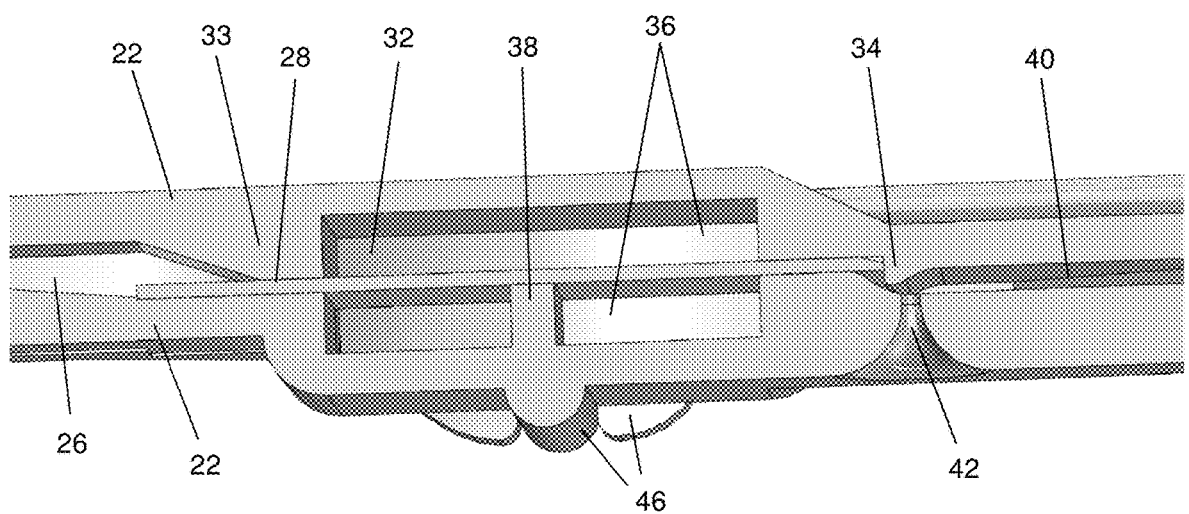
FIG. 7 shows a detailed view of box 7 as shown in FIG. 6.

The device 10 is typically formed from two separate pieces, a top 22 and a bottom 24, which couple together in a removable way, such as by friction or snap fit. In coupling together, the top 22 and bottom 24 of the device form a flow channel 26, best shown in FIGS. 5-7. The device 10 typically comprises a separation membrane 28, which functions to separate red blood cells from plasma, and an absorbent membrane 30, which functions to absorb the plasma and keep it separate from the red blood cell containing separation membrane 28, both of which are lateral flow membranes. FIG. 5 shows the flow channel without the separation membrane 28 and absorbent membrane 30 in place, while FIGS. 6 and 7 show the flow channel with the separation membrane 28 and absorbent membrane 30 in place.

The flow channel 26 begins at the proximal end 12 of the device 10, where a blood sample enters the flow channel 26. The flow channel 26 comprises a membrane region 32, which opens up into a chamber having a larger cross-section than the preceding upstream region of the flow channel 26. The flow channel 26 comprises a ramp 33 just proximal to the membrane region 32, which assists in both holding the membrane in place and encouraging the blood sample to enter the membrane. By reducing the volume of the flow channel 26 at certain regions, the separation membrane 28 is able to draw in the blood sample with capillary force. It can be seen in the drawings that the flow channel is not completely flat and flows downhill as it moves downstream in the direction of the sample flow. In this way, there are both capillary forces and gravitational forces acting on the sample as it moves downstream. Thus, typically, the separation membrane 28 is held in the flow channel 26 so that the blood sample enters from the top side of the separation membrane 28. Blood will not begin flowing into the separation membrane 28 until a sufficient volume is drawn into the flow channel upstream of the separation membrane 28. In this way, the device will only operate when a sufficient amount of blood is applied to complete the plasma separation and collection.

As noted, the membrane region 32 of the flow channel 26 opens up to have a larger volume than the remainder of the flow channel 26. When the separation membrane 28 is in place, capillary traps 36 are created that force the blood to travel entirely through the separation membrane 28. This avoids blood flow in and around, rather than through, the separation membrane 28 and promotes full separation of the plasma from the blood sample so that red blood cells are retained in the separation membrane 28 and only plasma continues to flow through the flow channel 26. The membrane region 32 may comprise one or more supports 38 that assist in keeping the separation membrane 28 in place and reduce sagging that may occur once the separation membrane 28 is saturated with blood.

Following the membrane region 32, the flow channel 26 again constricts at constriction 34 to both hold the separation membrane 28 in place and encourage continued downstream flow of the plasma into a chamber 40, which typically does not contain any membranes and is simply an open region within the flow path. The chamber 40 is typically of smaller cross-section than the proximal region of the flow path. To ensure smooth plasma flow into the chamber 40 this region must have a greater capillary force to draw the sample from the upstream region of flow channel 26. In quantitative devices, the chamber 40 is of a predefined volume and is designed so that only that volume will enter the absorbent membrane 30 through use of a proximal vent 42 in the bottom wall of the chamber 40. The vent 42 has a capillary force that is equal to or greater than that of the chamber 40 but less than that of the absorbent membrane 30. In this way, the chamber 40 will fill with plasma without air bubbles from the vent 42 until the front of the plasma touches the absorbent membrane 30, which is held in place in a plasma collection region 44. Once this happens, the plasma will be drawn into the absorbent membrane 30 with sufficient force that the vent 42 will allow air to enter the chamber 40 rather than further plasma from the separation membrane 28. This will result in a defined volume of plasma in the absorbent membrane 30 and an air bubble in the chamber 40, the air bubble effectively acting as a barrier against further flow.

Once the test is complete, the device 10 can be easily separated by holding the top 22 and pushing on the handle 18, so that the absorbent membrane 30 can be dried and shipped, as required, or the device can be shipped directly to a lab for plasma testing.

As noted, the device 10 is typically formed by mated top 22 and bottom 24 portions, as shown in FIGS. 3 to 7, for ease of manufacturing and insertion and removal of the separation membrane 28 and the absorbent membrane 30. The device 10 could also be formed as a single unit. As shown, there are mated friction-fit components 46 and 48 that hold the top 22 and bottom 24 portions together. As shown, these components allow the top 22 and bottom 24 to pivot with respect to one another, therefore facilitating opening of the device 10 to remove the absorbent membrane 30 for testing.

FIGS. 8 to 29 show a second aspect of the device 100, which also comprises a proximal end 112 and a distal end 114. The distal end 114 comprises a handle 118. The device 100 typically comprises an open window 120 which allows for visual inspection of the sample so the user can see when the absorbent membrane 130 is wet. This gives a reliable indication of when the collection of plasma is complete. In optional embodiments, the absorbent membrane 130 may comprise a colorant that mobilizes with the plasma front, such as a simple food dye or known colored reagent that would not otherwise affect the test. In this way, movement of the front is easily visualized. Furthermore, if the collected plasma is in a quantity that is insufficient to fill the entire absorbent membrane 130, the filled area will be easily identified from the colored front, especially when the absorbent membrane 130 is dried. The plasma front, when wet, may be visible even without color, however, when a colorant is further included, it assists in identifying the front of plasma even after the plasma has dried and is otherwise difficult to visualize. In aspects, this mobile colorant serves as a quality control feature where a lab to which the sample has shipped can confirm whether the plasma filled the entire absorbent membrane 130 as intended or whether the test was incomplete. The absorbent membrane 130 can be weighed, cut at the colored front, and weighed again in order to still retain a quantitative test.

Figure 12:
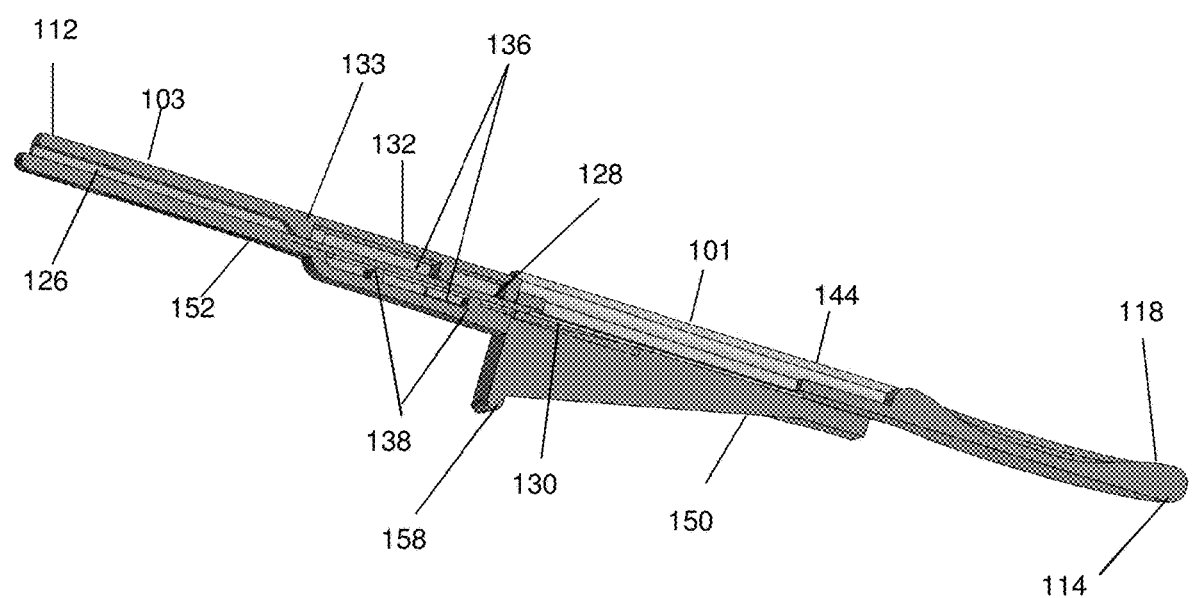
FIG. 12 shows a cross-section view along line 12-12 of the device of FIG. 8, with separation and absorbent membranes.

The window 120 also allows for efficient and faster drying of the absorbent membrane 130 containing the separated plasma. Furthermore, the presence of the window 120 means that the absorbent membrane 130 is open to the air, and therefore no vent 42, as previously described for device 10, is typically included. A vent may be optionally included, however, if desired. FIG. 12 shows a flow channel 126 with the separation membrane 128 and absorbent membrane 130 in place.

Figure 8:
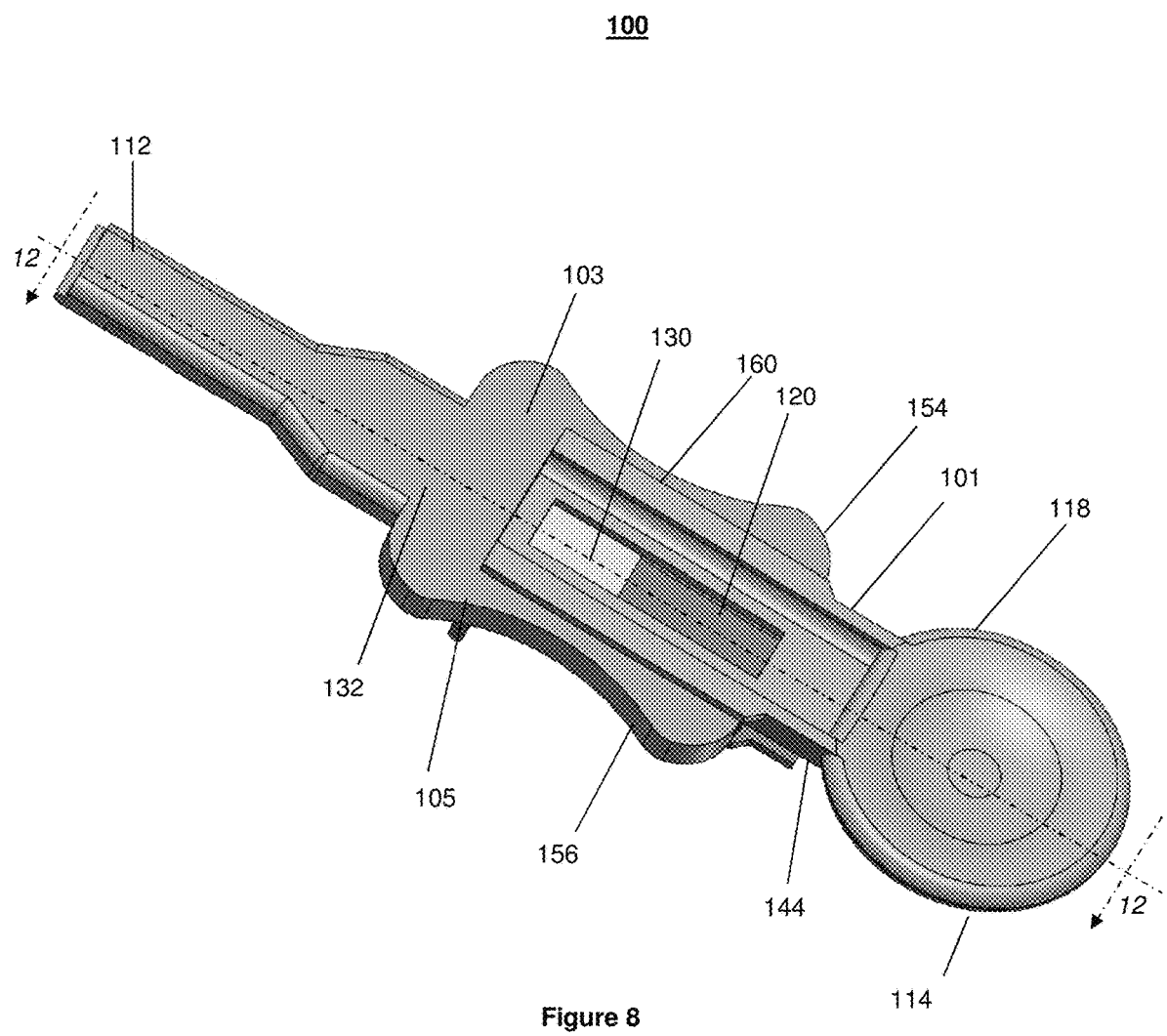
FIG. 8 shows a top perspective view of a second aspect of a device described herein.
Figure 9:
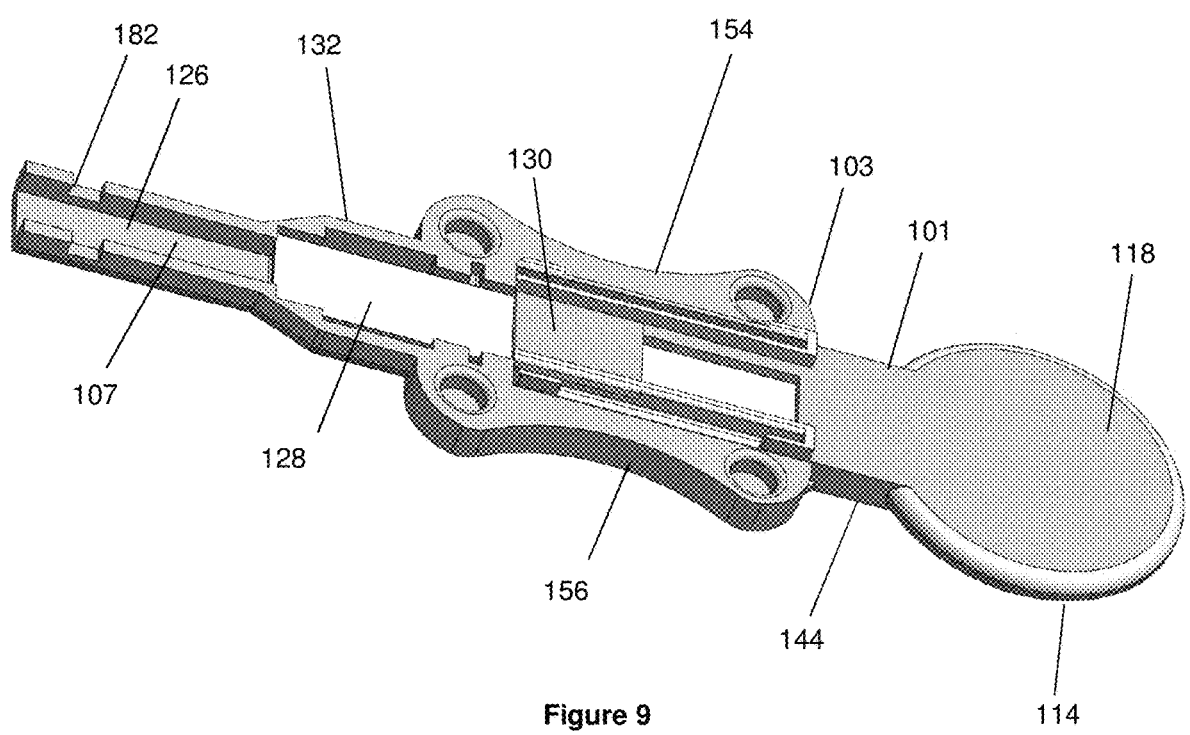
FIG. 9 shows a bottom perspective view of the device of FIG. 8 without a back portion attached.
Figure 10:
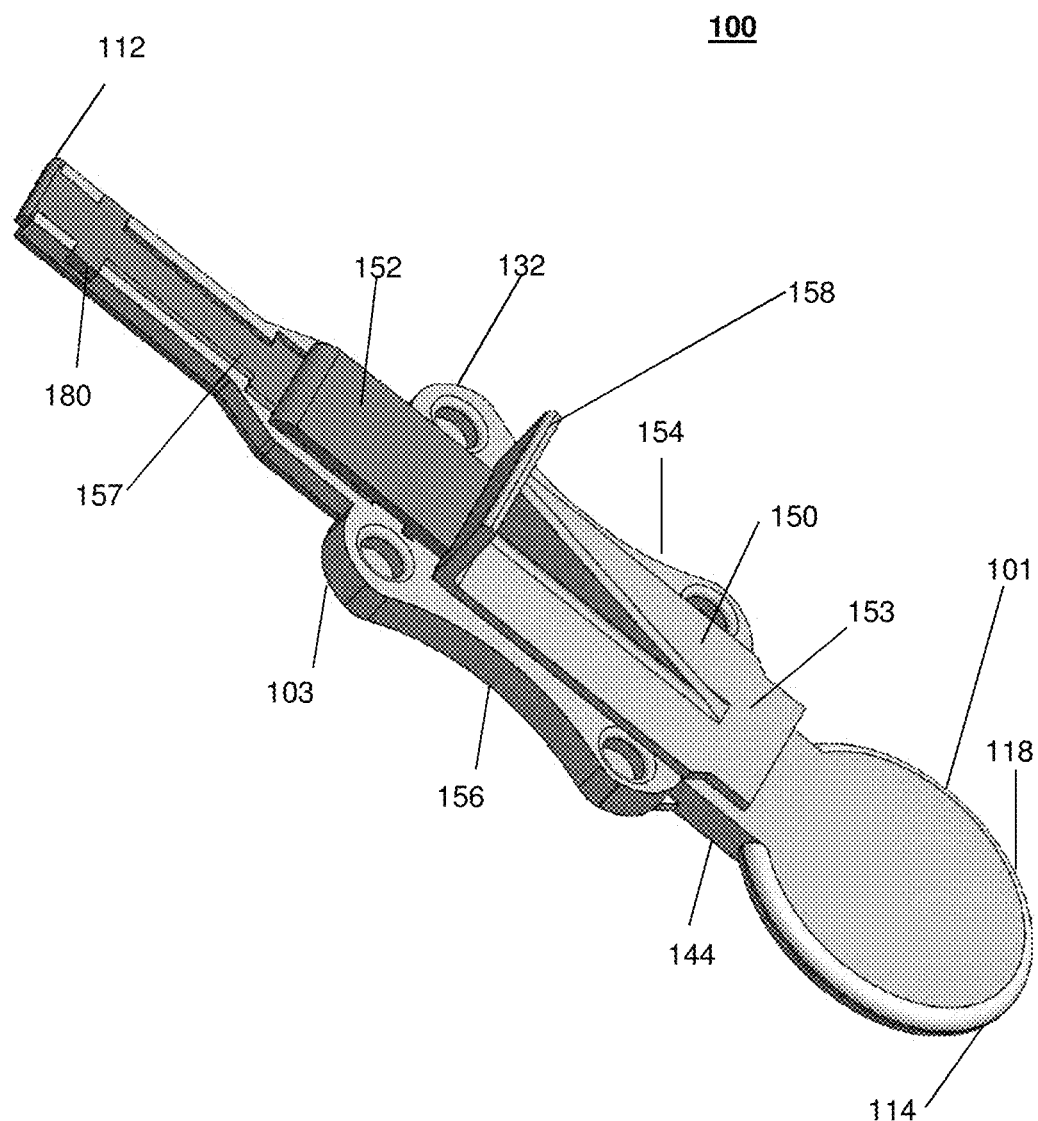
FIG. 10 shows a bottom perspective view of the device of FIG. 9 with the back portion attached.

Also like the device 10 of the first aspect, the device 100 typically comprises a flow channel 126, a separation membrane 128, and the absorbent membrane 130, both of which are lateral flow membranes. The membranes 128, 130 are in fluid communication with the flow channel 126, and with each other in a first orientation, such as is shown in FIG. 8. In a second orientation, such as is shown in FIG. 11, the flow of plasma can be impeded (such as slowed down, stopped, or blocked) by physically taking the membranes away from one another, resulting in the membranes 128, 130 no longer being in fluid communication with each other.

Figure 11:
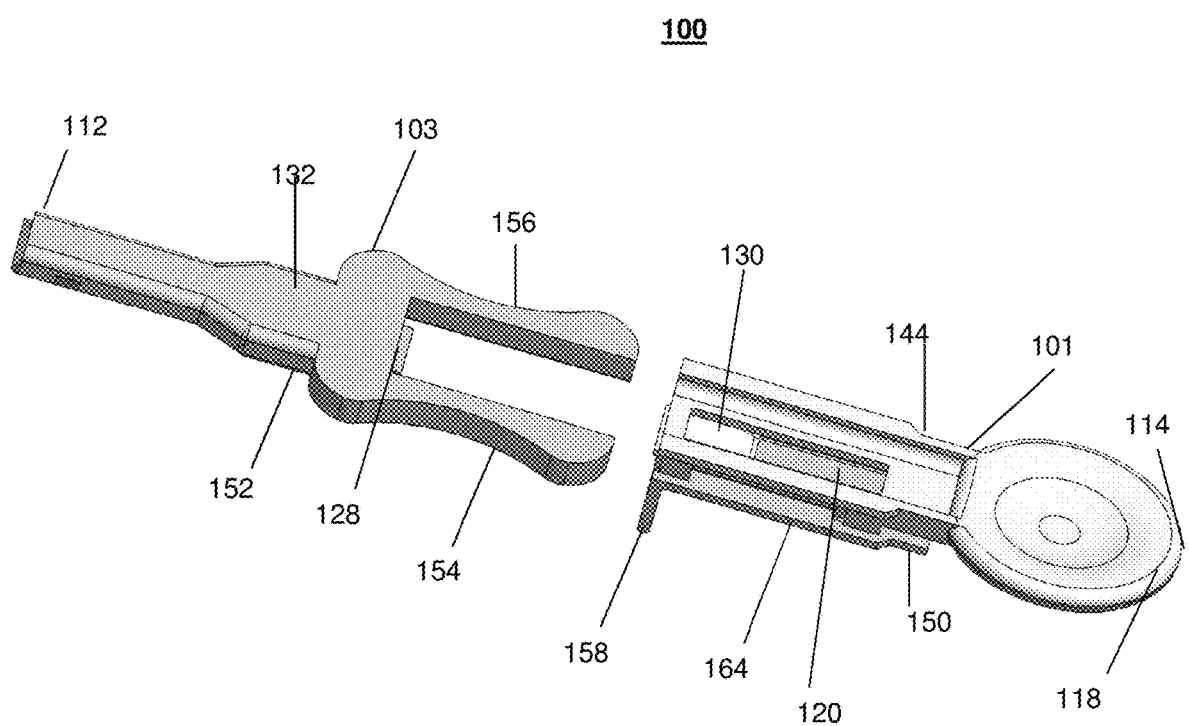
FIG. 11 shows a top perspective view of the device of FIG. 8 in a separated configuration.

As best seen in FIG. 11, the device 100 comprises two separate regions, a plasma collection region 144 and a membrane region 132, which couple together in a removable way, such as by friction or snap fit. This connection of the plasma collection region 144 and the membrane region 132 reduces unintentional separation of the plasma collection region 144 and the membrane region 132 when the device 100 is fully assembled. This is advantageous in that the coupling of the two regions 132, 144, or the components that are coupled to produce the plasma collection region 144 and the membrane region 132, as described below, do not need an adhesive for attachment to each other. Not only does this allow for the regions 132, 144 (or the components thereof, described below) to be easily assembled and disassembled, but it also provides for less associated mess (e.g., dealing with a sticky adhesive product) for the user.

Figure 13:
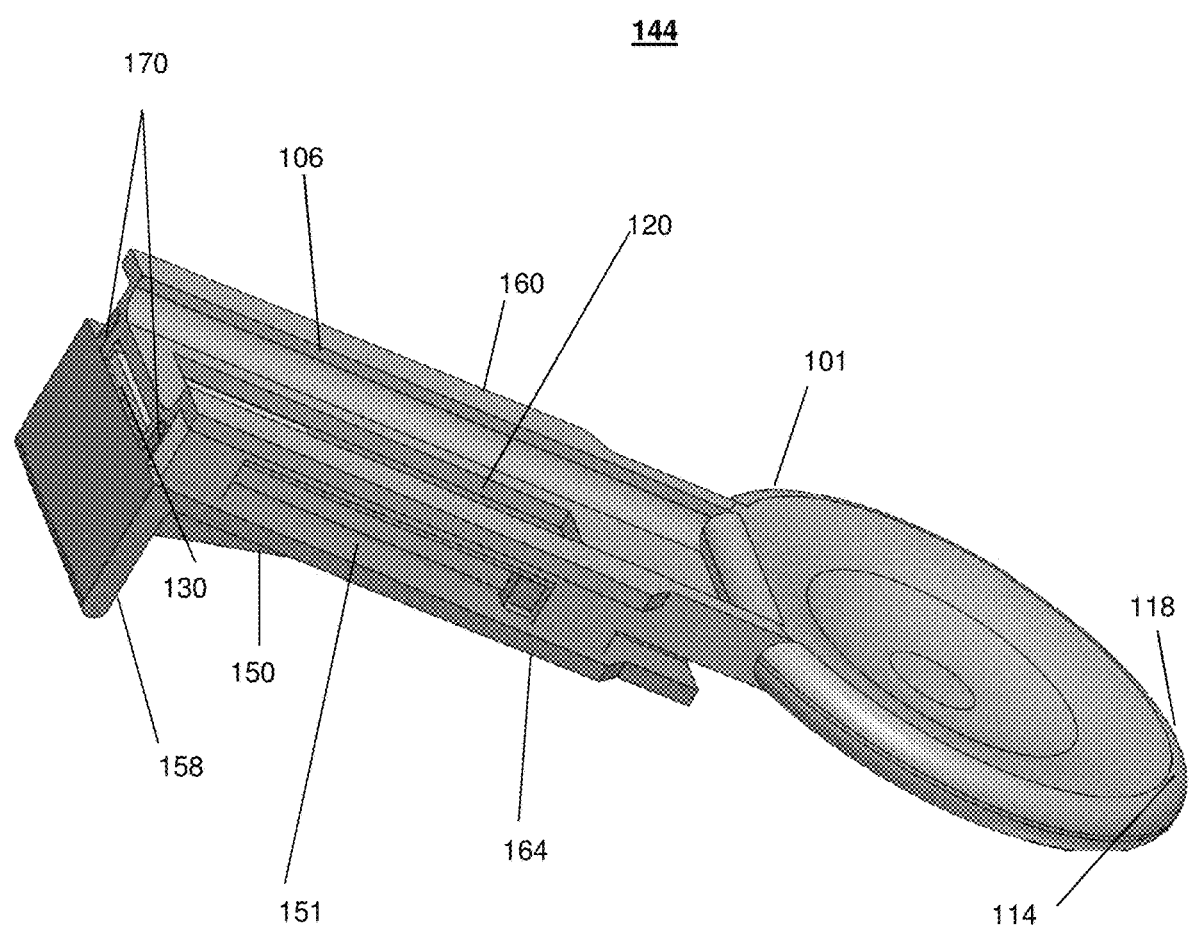
FIG. 13 shows a top perspective view of a plasma collector portion of the device of FIG. 8 in closed configuration.
Figure 14:
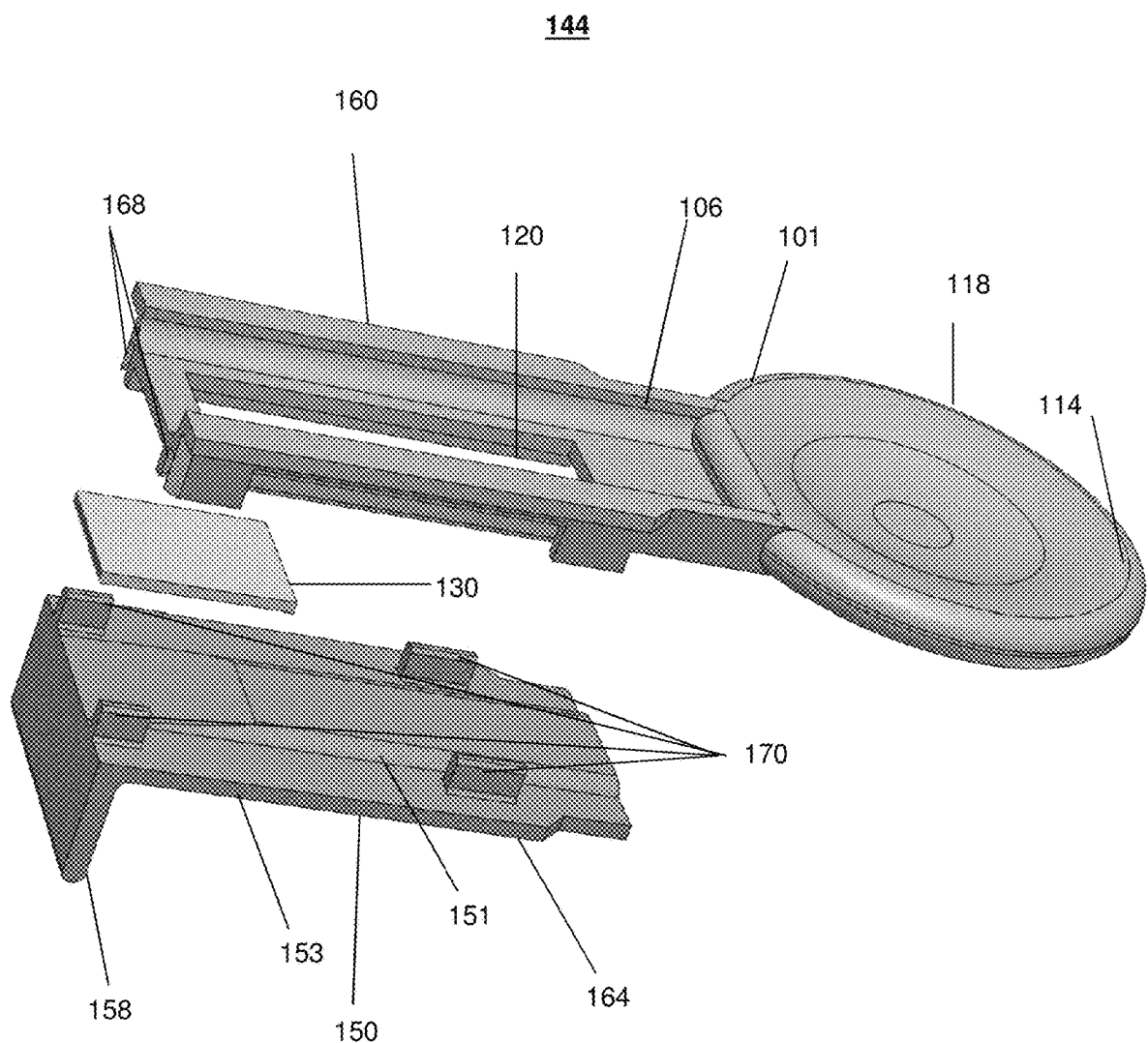
FIG. 14 shows a top perspective exploded view of a plasma collector portion of the device of FIG. 8 with an absorbent membrane.
Figure 15:
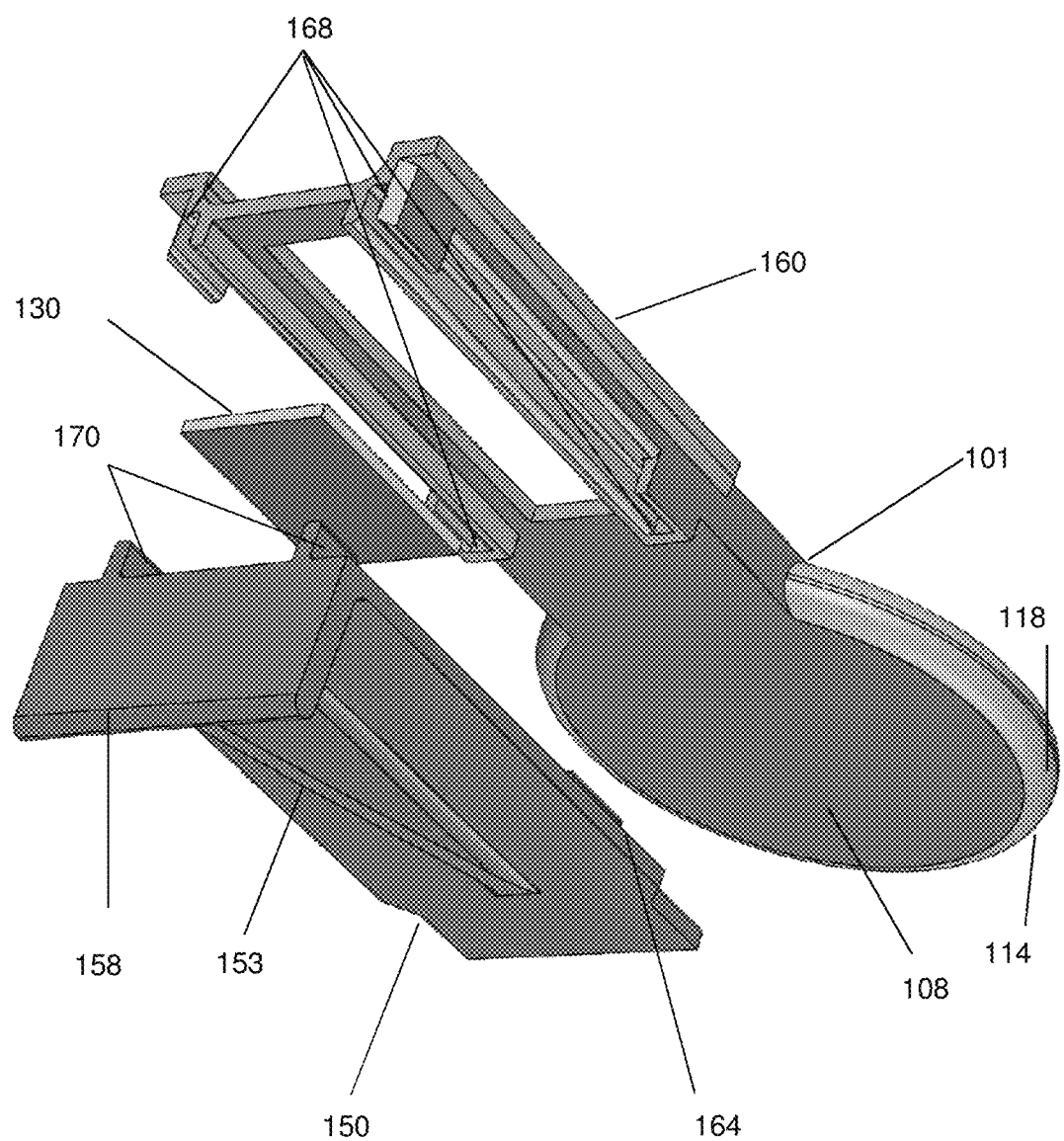
FIG. 15 shows a bottom perspective exploded view of a plasma collector portion of the device of FIG. 8 with an absorbent membrane.
Figure 16:
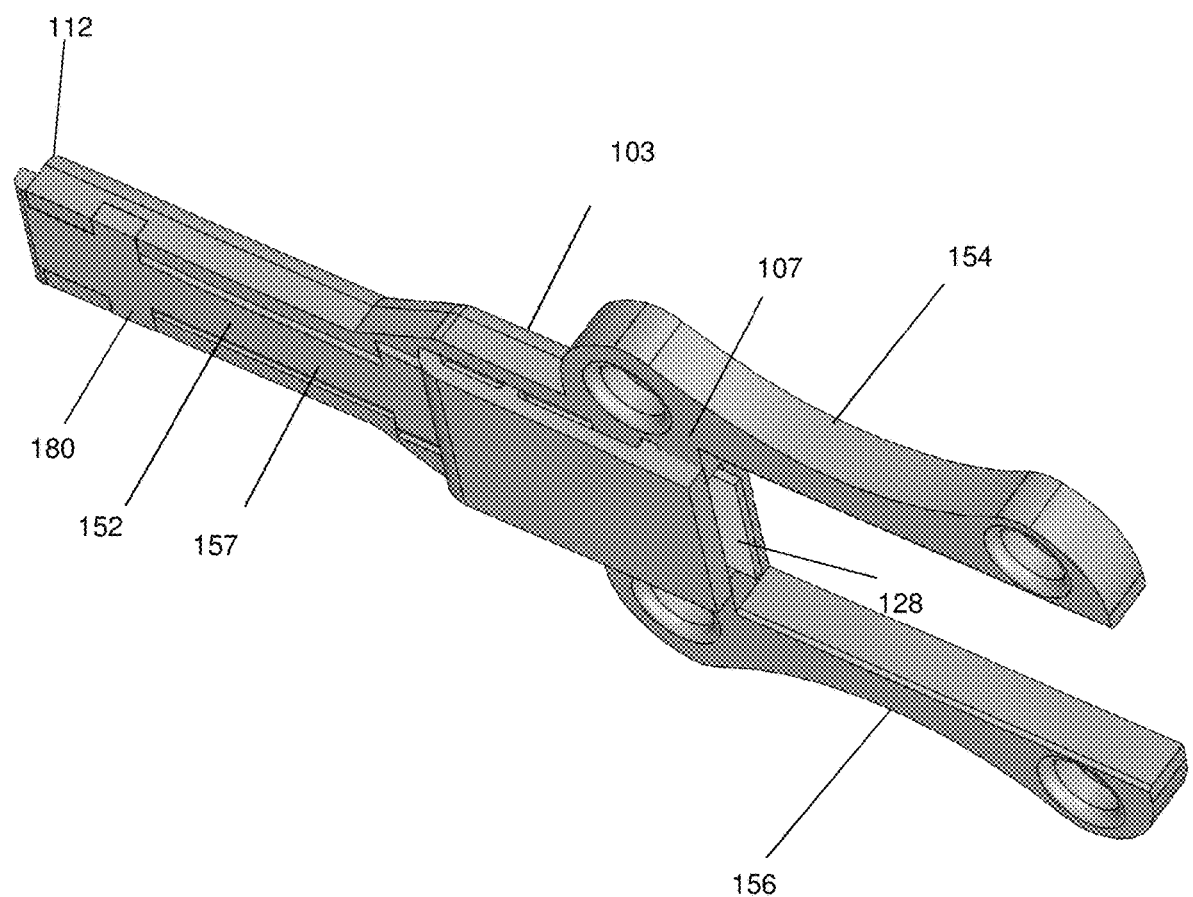
FIG. 16 shows a bottom perspective view of a plasma separator portion of the device of FIG. 8 in closed configuration.

FIGS. 13-15 show the plasma collection region 144 in more detail. The plasma collection region 144 comprises a top portion 101 and a bottom portion 150 which removably couple together, thereby forming the assembled plasma collection region 144 for holding the absorbent membrane 130 (FIG. 14). In aspects, the plasma collection region 144 comprises the handle 118 at the distal end 114 of the device 100.

The top portion 101 of the plasma collection region 144 has a top surface 106 (FIG. 14) and a bottom surface 108 (FIG. 15). In aspects, the top surface 106 comprises the window 120 for visual inspection and/or separation or removal of the absorbent membrane 130. The top surface 106 comprises lateral projections 160, which may span a length of the top portion 101 or may span only a portion thereof. The lateral projections 160 are for coupling with a top surface 105 of the membrane region 132, when the device is to be assembled and used.

The bottom surface 108 of the top portion 101 has grooves 168 which may span along a length of the bottom surface 108 or along a portion thereof. The lengths of the projections and grooves, 160 and 168, respectively, including their position on the surfaces described herein, are not considered limiting.

The bottom portion 150 of the plasma collection region 144 comprises a top surface 151 and a bottom surface 153. The top surface 151 comprises projections 170, extending upwardly from the top surface 151, for example, which register with the grooves 168 of the bottom surface 108 of the top portion 101. The bottom portion 150 may further comprise lateral projections 164 to facilitate connection with the top portion 101. When the top portion 101 and the bottom portion 150 are connected through, for example, the grooves 168 and projections 170, the absorbent membrane 130 is held in place in the plasma collection region 144. Once disconnected from the membrane region 132, the plasma collection region 144 containing the absorbent membrane 130 can be sent to the laboratory for further testing and analysis without having to remove the absorbent membrane 130 from the membrane plasma collection region 144. Alternatively, the absorbent membrane 130 can be removed from the plasma collection region 144, dried, and sent to a laboratory for further testing.

In aspects, the bottom portion 150 has a stand member 158 connectable to the bottom surface 153. The stand member 158 is useful for resting the device 100 on a table, for example. In aspects, the stand member 158 has an inclined surface, which facilitates the downward movement of the plasma from the separation membrane 128 to the absorbent membrane 130. The stand member 158 is also advantageous in providing a "hands free" option for the user to apply the blood sample to the device 100 without holding the device in one hand as described herein.

Figure 17:
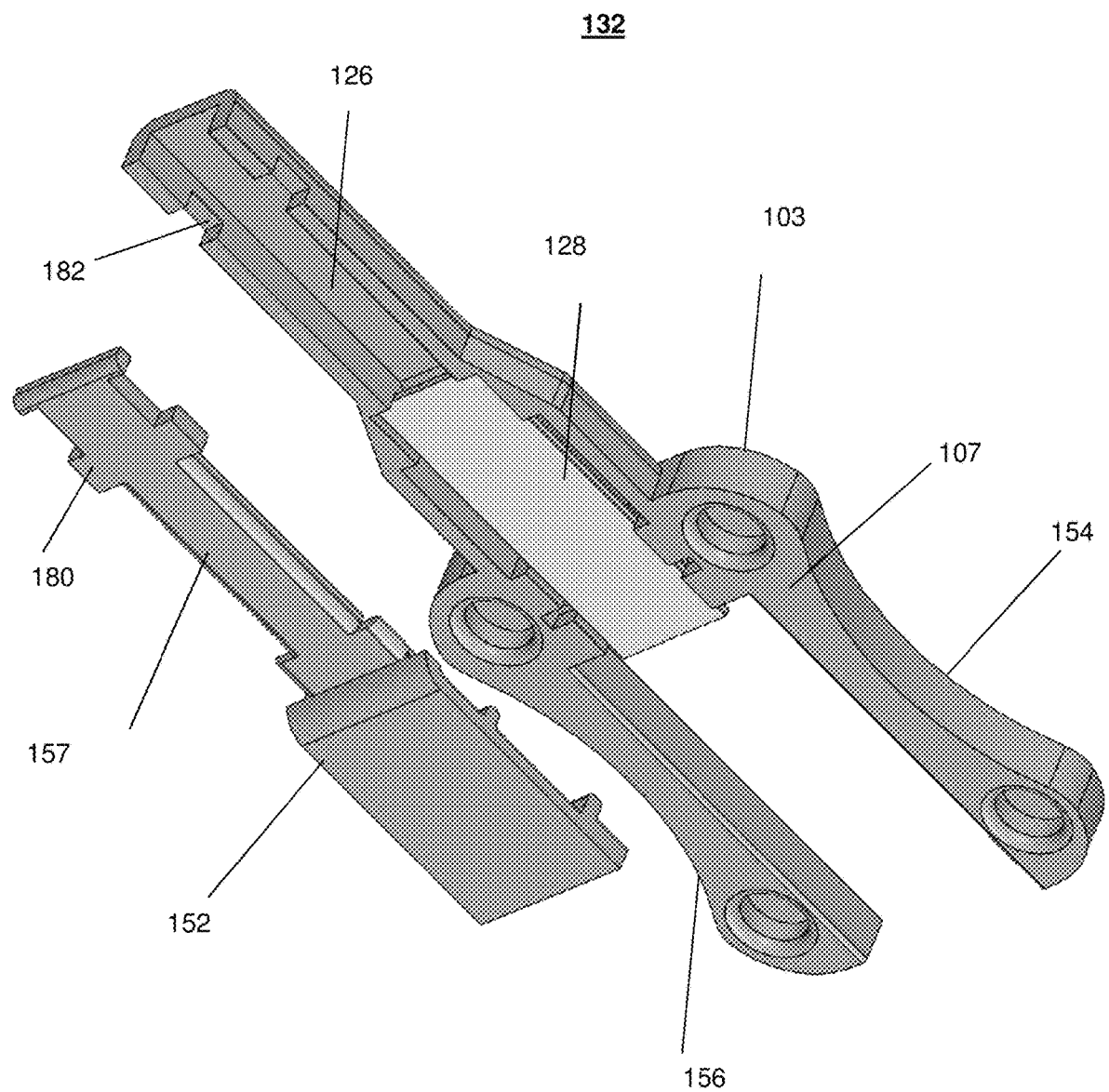
FIG. 17 shows a bottom perspective exploded view of a plasma separator portion of the device of FIG. 8 with a separation membrane inserted.
Figure 18:
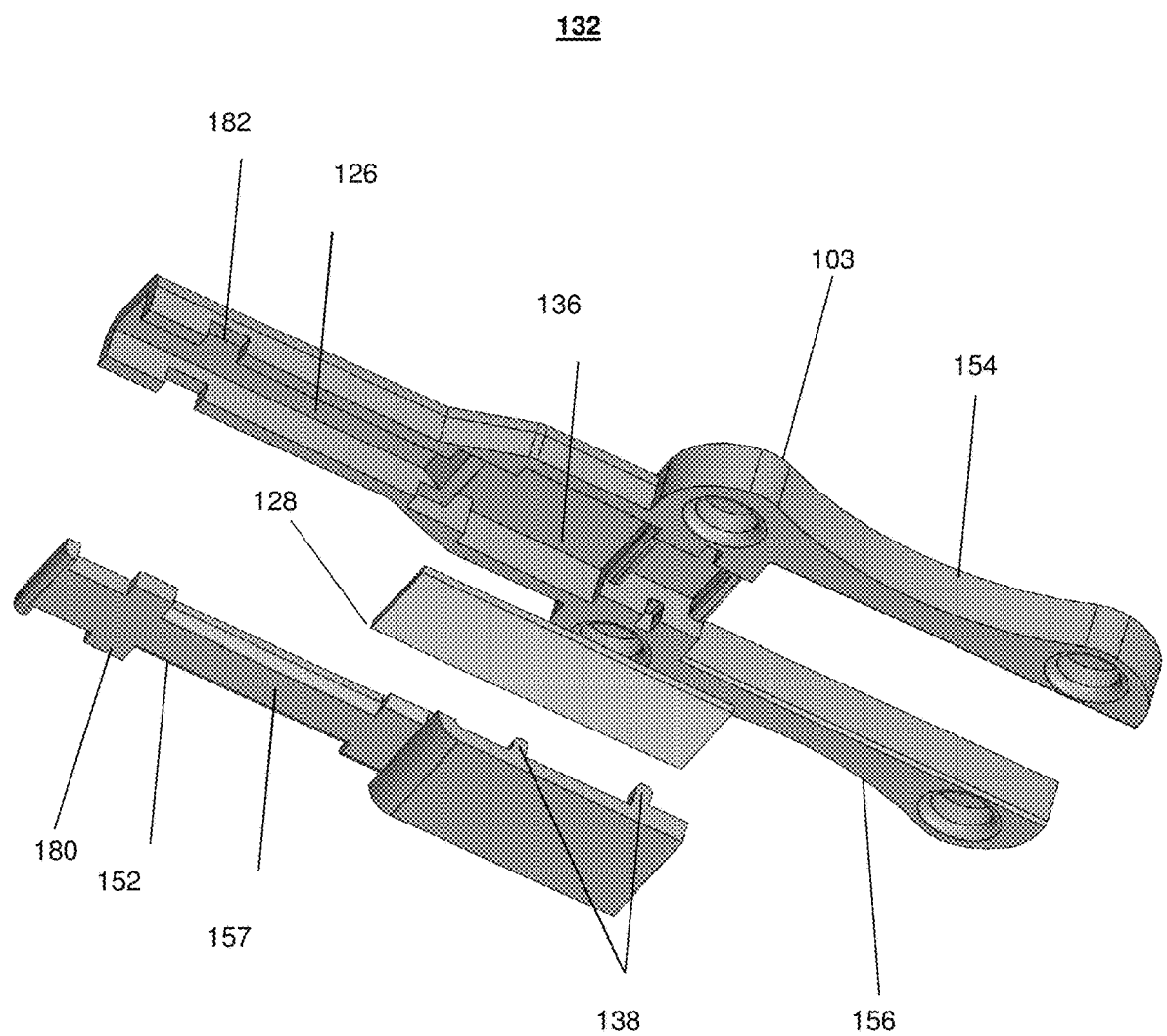
FIG. 18 shows a bottom perspective exploded view of a plasma separator portion of the device of FIG. 8 with separation membrane.
Figure 19:
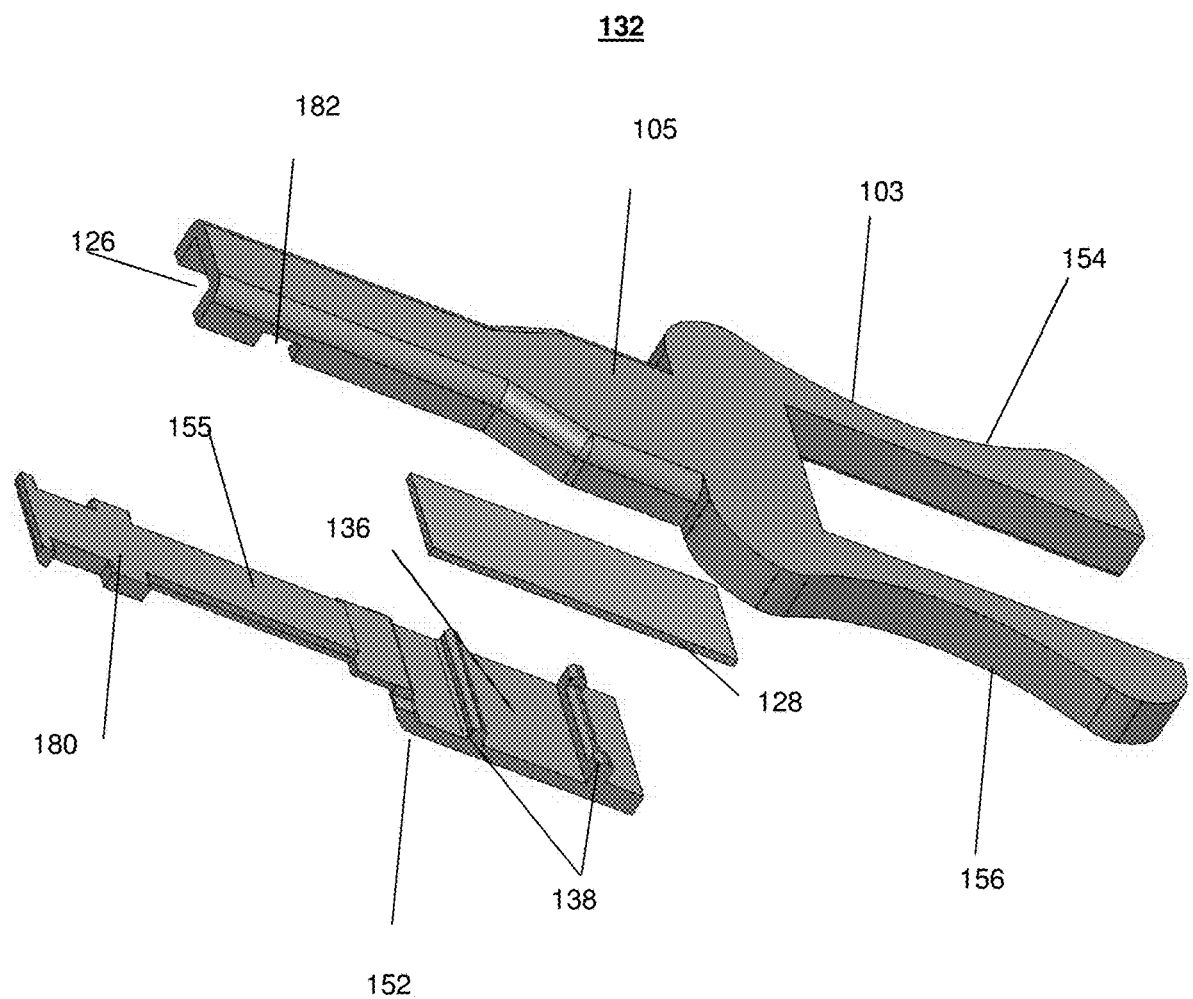
FIG. 19 shows a top perspective exploded view of a plasma separator portion of the device of FIG. 8 with separation membrane.

FIGS. 16-19 and 27-29 show the membrane region 132 of the device 100 in more detail. The membrane region 132 comprises a top portion 103 and a bottom portion 152 which also removably couple together, thereby forming the assembled membrane region 132 for holding the separation membrane 128 (FIG. 17).

The top portion 103 of the membrane region 132 has a top surface 105 (FIG. 19) and a bottom surface 107 (FIG. 17). The top surface 105 comprises arm members 154, 156 for surrounding a portion of, and engaging with, the plasma collection region 144 when the device 100 is assembled for use. The arms 154, 156 can be of any shape so long as they register with the plasma collection region 144 to removably couple the plasma collection region 144 and the membrane region 132 together. For example, as described above, the top surface 105 of the membrane region 132 interacts with the lateral projections 160 of the plasma collection region 144 to form a removable coupling between the plasma collection region 144 and the membrane region 132.

The bottom surface 107 of the top portion 103 has grooves 182 which may span a length of the bottom surface 107 or span a portion thereof. The lengths of grooves 182, as well as their position on the surfaces described herein, are not considered limiting, so long as they function to removably couple the top portion 103 to the bottom portion 152. The bottom portion 152 of the membrane region 132 comprises a top surface 155 and a bottom surface 157. The top surface 155 may comprise supports 138 which assist in keeping the separation membrane 128 in place and reduce sagging that may occur once the separation membrane 128 is saturated with blood, as was described for device 10.

The bottom portion 152 also comprises lateral projections 180 which register with the grooves 182 of the bottom surface 107 of the top portion 103. When the top portion 103 and the bottom portion 152 are connected through, for example, the grooves 182 and projections 180, the separation membrane 128 is held in place in the assembled membrane region 132.

It would be readily apparent to those skilled in the art what other known methods of providing releasable (e.g., removable) attachments are possible within the scope described herein, with respect to removable coupling between the plasma collection region 144 and the membrane region 132 and/or between their top portions 101, 103, and bottom portions 150, 152 (e.g., the aforementioned "components"), respectively.

As was described for device 10, as the sample flows through the flow channel 126, the flow channel 126 of the device 100 also opens up to have a larger volume than the remainder of the flow channel 126. Also similar to device 10, when the separation membrane 128 is in place, the creation of capillary traps 136 force the blood to travel entirely through the separation membrane 128. This avoids blood flow in and around, rather than through, the separation membrane 128 and promotes full separation of the plasma from the blood sample so that red blood cells are retained in the separation membrane 128 and only plasma continues to flow through the flow channel 126.

In coupling together, the top portion 103 and bottom portion 152 of the membrane region 132 form the flow channel 126 which, like the device 10, begins at the proximal end 112 of the device 100. The flow channel 126 may comprise a ramp 133 which functions similarly to that of device 10. The description of the flow channel 126 of device 100 is the same as that for device 10 and therefore need not be repeated for device 100.

Typically, the separation membrane 128 is held in the flow channel 126 so that the blood sample enters from a top side of the separation membrane 128. As can be seen in FIG. 12, the top surface 155 of the bottom portion 152 of the membrane region 132 is substantially flush with the top side of the separation membrane 128, allowing for the blood sample to enter the top side of the membrane 128. As was described for device 10, blood will not begin flowing into the separation membrane 128 until a sufficient volume is drawn into the flow channel upstream of the separation membrane 128. In this way, the device 100 will only operate when a sufficient amount of blood is applied to complete plasma separation and collection.

FIGS. 20 to 29 show some modifications to the design of the device 100, in which additional features are included to assist in holding the separation membrane 128 and the absorbent membrane 130 in place, as well as reducing evaporation and improve assembly.

Figure 20:
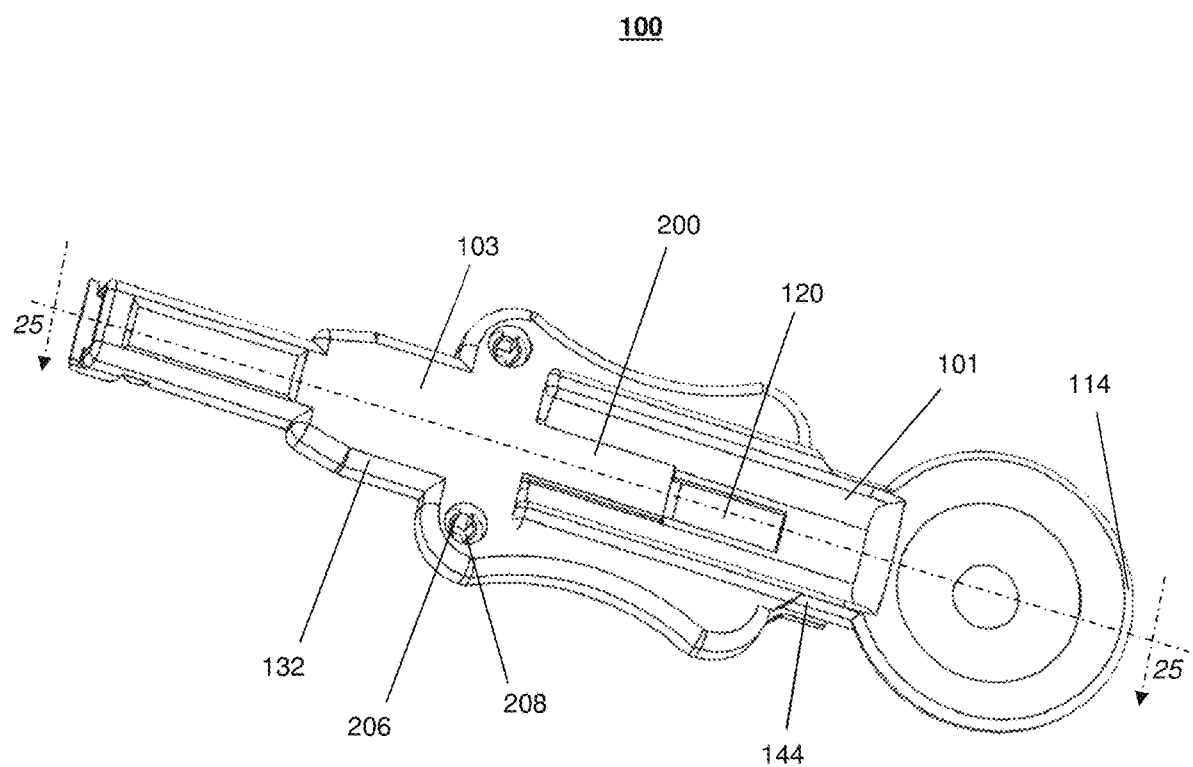
FIG. 20 shows a top perspective view of a second aspect of a device described herein.
Figure 21:
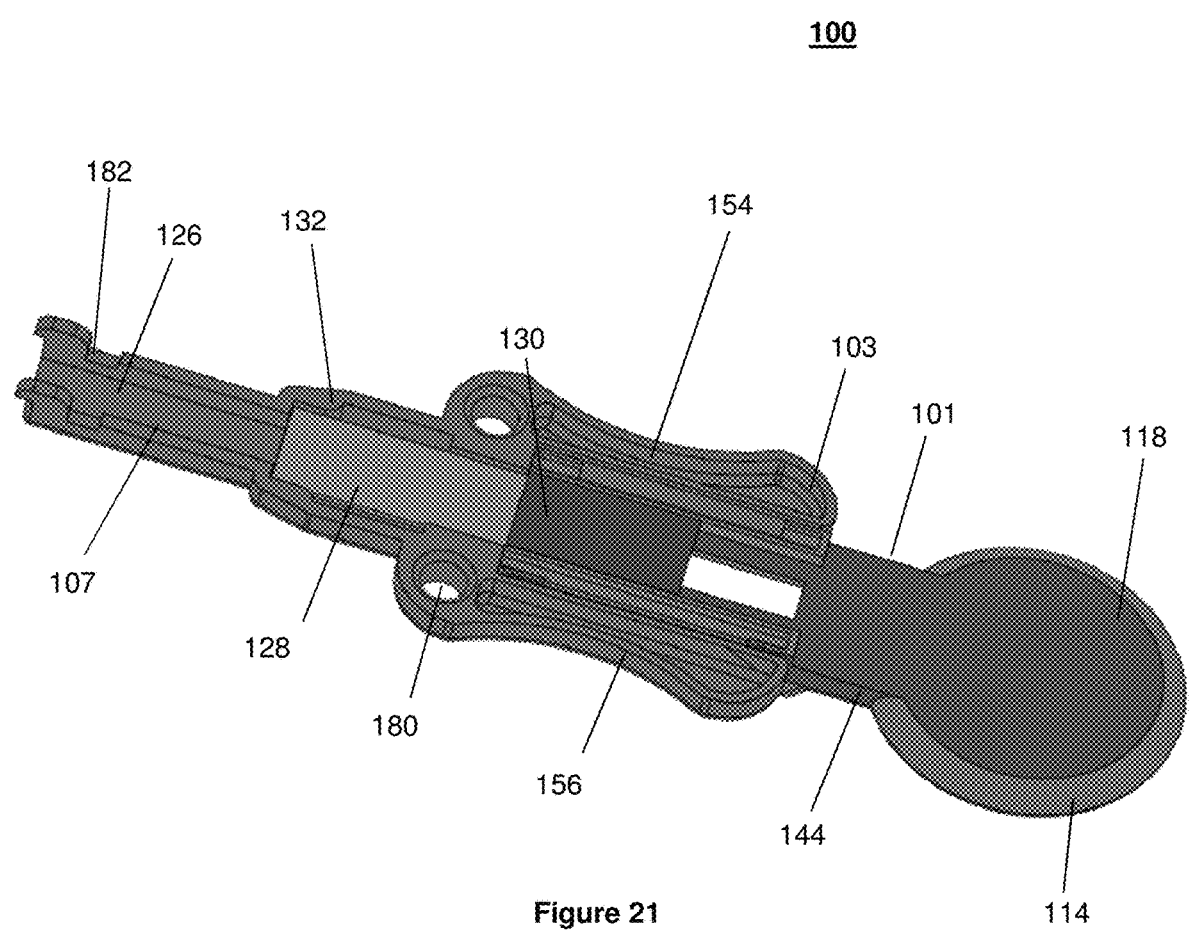
FIG. 21 shows a bottom perspective view of the device of FIG. 20 without a back portion attached.
Figure 22:
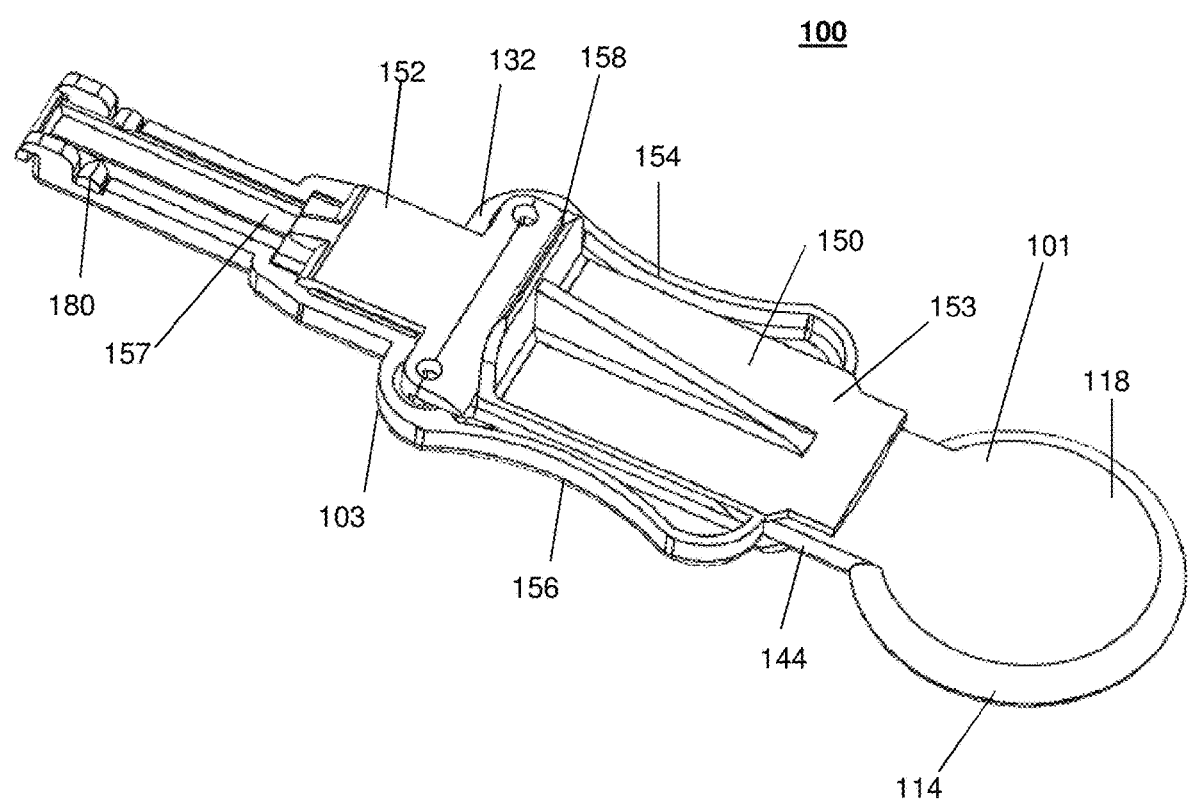
FIG. 22 shows a bottom perspective view of the device of FIG. 20 with the back portion attached.

Turning to FIG. 20, a top view of the device 100 is shown. The components are all generally the same as those identified in FIGS. 8 to 19. In FIG. 20, the top portion 103 of the membrane region 132 is shown with a tongue 200, which extends towards the distal end 114 and covers part of the window 120 and absorbent membrane 130. In doing so, the tongue 200 reduces premature evaporation of plasma from the window 120 and thereby improves flow and increases the plasma volume accuracy in the absorbent membrane 130.

Figure 23:
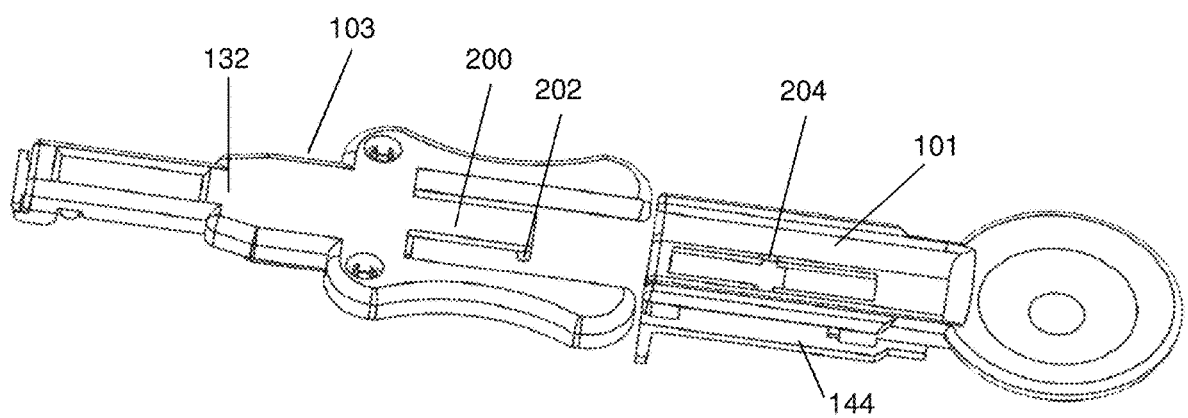
FIG. 23 shows a top perspective view of the device of FIG. 20 in a separated configuration.
Figure 24:
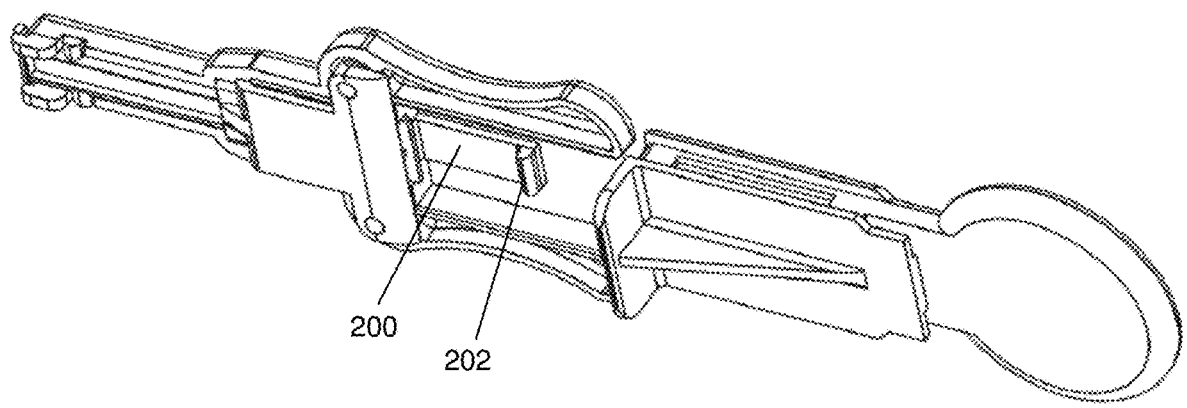
FIG. 24 shows a bottom perspective view of the device of FIG. 20 in a separated configuration.

As shown in FIGS. 20 and 23, tongue 200 comprises a protrusion 202 that engages with a corresponding void 204 in the window 120 of the top portion 101 of the plasma collection region 144. Tongue 200 assists in holding the membrane region 132 and the plasma collection region 144 in proper position for use and also reduced evaporation, as noted above.

Figure 28:
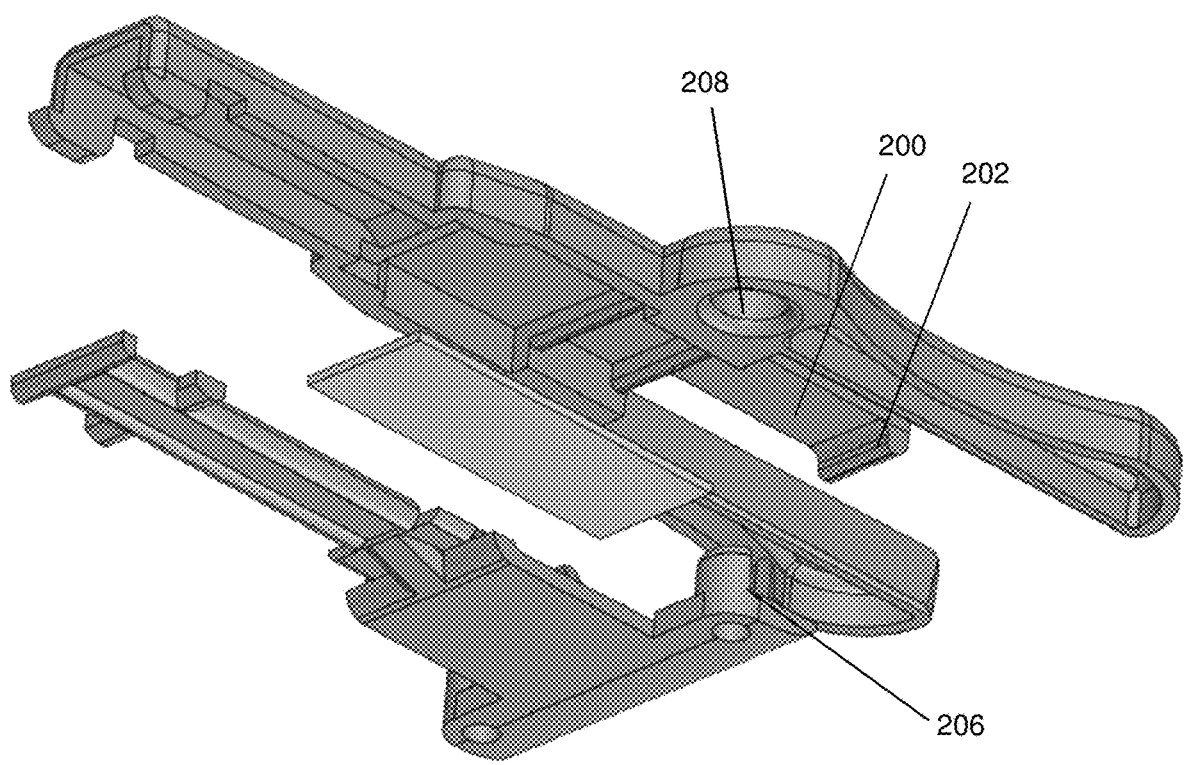
FIG. 28 shows a bottom perspective exploded view of a plasma separator portion of the device of FIG. 20 with a separation membrane inserted.

FIG. 28 shows an alternative method of engaging the top portion 103 and the bottom portion 152 of the membrane region 132 of the device 100. In this embodiment, the bottom portion 152 is provided with two posts 206 that engage with corresponding cavities 208 in the top portion 152 of the device 100. These can engage with a snap-fit or a friction-fit, for example.

Figure 25:
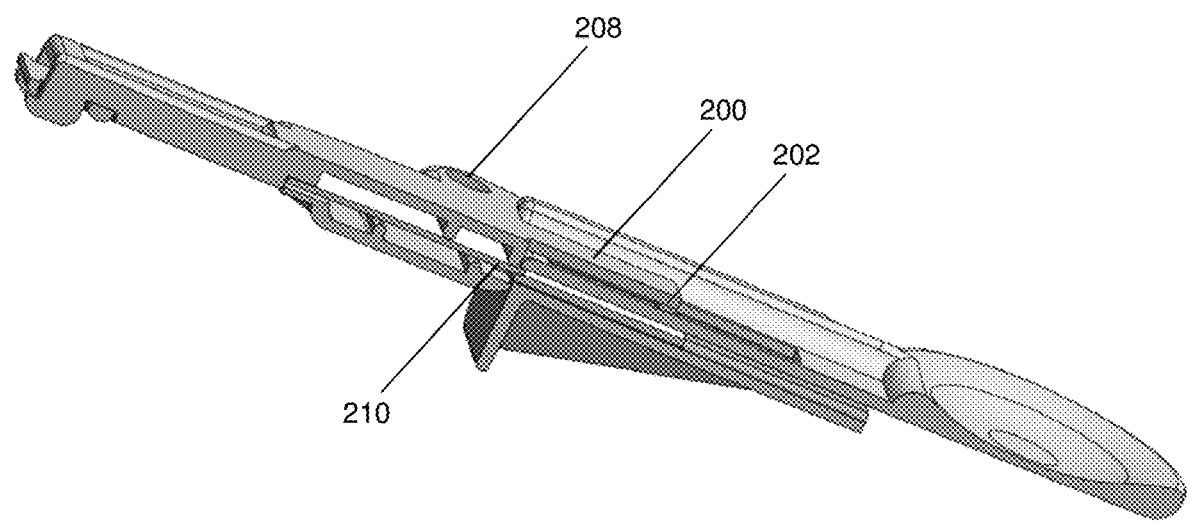
FIG. 25 shows a cross-section view along line 25-25 of the device of FIG. 20, with separation and absorbent membranes.
Figure 26:
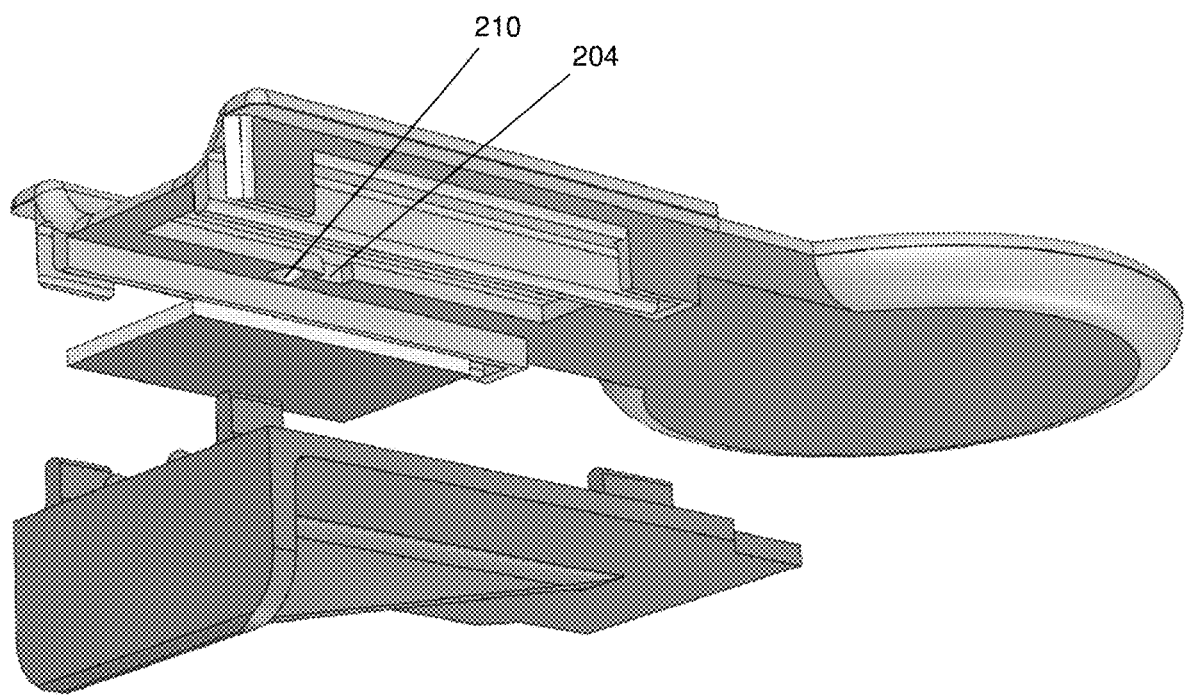
FIG. 26 shows a bottom perspective exploded view of a plasma collector portion of the device of FIG. 20 with an absorbent membrane.
Figure 27:
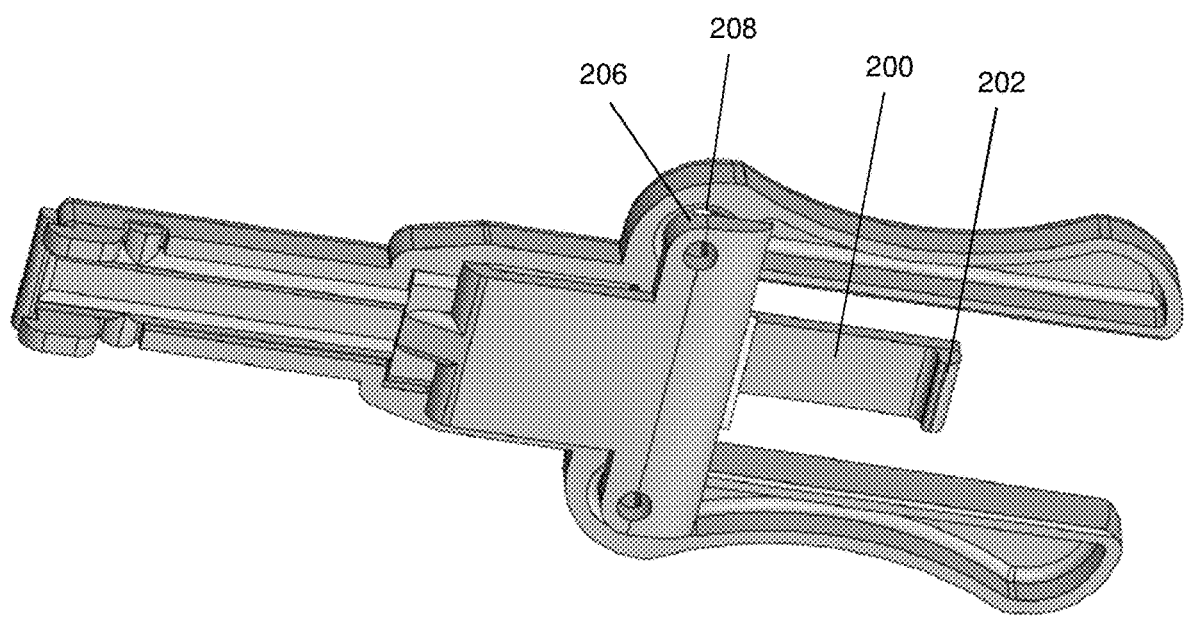
FIG. 27 shows a bottom perspective view of a plasma separator portion of the device of FIG. 20 in closed configuration.
Figure 29:
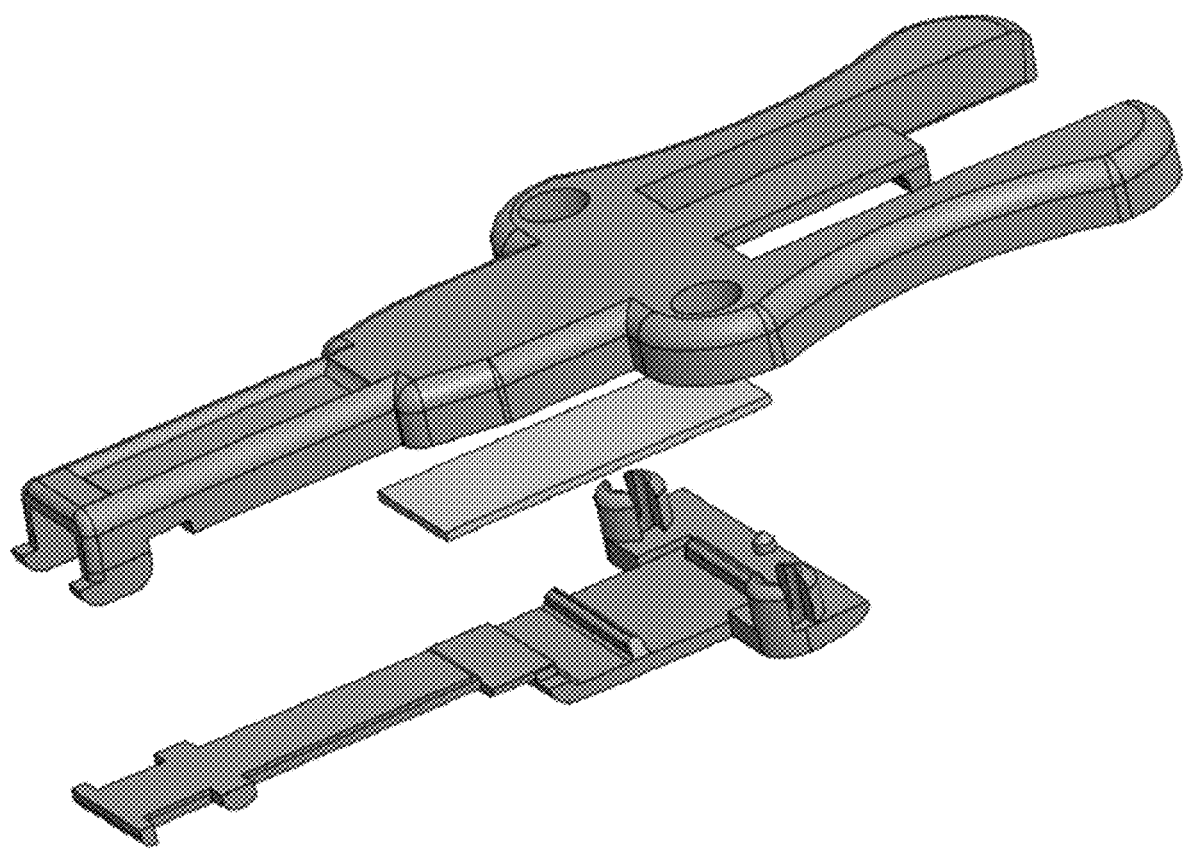
FIG. 29 shows a top perspective exploded view of a plasma separator portion of the device of FIG. 20 with a separation membrane.

FIGS. 25, 26, and 29 show pins 210 that assist in holding the separation membrane 128 and/or the absorbent membrane 130 in position. These simply bias slightly against the membranes 128 and/or 130, thereby reducing the potential for movement in use or when the membrane region 132 and the plasma collection region 144 are separated.

The absorbent membrane 130 is of a predefined volume and is designed so that only that volume will enter the absorbent membrane 130, which is held in place in a plasma collection region 144. Once plasma reaches an edge of the separation membrane 128, the plasma will be drawn into the absorbent membrane 130 by capillary forces. Depending on the orientation of the membranes 128, 130, for example, if the membranes 128, 130 are adjacent (lateral side-to-side) touching or if the membranes 128, 130 are overlapping, the plasma is drawn into an edge of the absorbent membrane 130 or to a top side of the absorbent membrane 130. Once the plasma is collected in the absorbent membrane 130, because the volume of the absorbent membrane 130 is known, a defined volume of plasma in the absorbent membrane 130 is provided.

Once the device 100 is assembled, the absorbent membrane 130 is housed in the plasma collection region 144 and the separation membrane 128 is housed in the membrane region 132. The membranes 128, 130 may be laterally associated with each (e.g., side-to-side contact between their edges) or they may be overlapped with each other (such as the absorbent membrane 130 overlapping the separation membrane 128, or vice versa). In aspects, the membranes form a contiguous surface for the flow of plasma. Regardless of their orientation, the membranes 128, 130 are in fluid communication with each other and in fluid communication with the flow channel 126. Whether the membranes 128, 130 overlap one another, or they contact each other at their edges, the flow of the plasma is continuous from the flow channel 126 through the membranes 128, 130. This facilitates the speed of flow of the plasma through the device 100. Advantageously, the association of the membranes 128, 130 with each other (for example, through adjacent lateral contact or through overlapping contact), allows forflow of plasma through the flow channel 126 (e.g., through the separation membrane 128 to the absorbent membrane 130) to be impeded or stopped completely by simply taking the membranes out of close physical contact.

In aspects, the membranes 128, 130 do not require adhesive connections between them (e.g., that they are physically connected to each other, such as, by way of a backing strip) when they are in the lateral adjacent orientation or an overlapping orientation. In this way, the devices 10, 100 (with respect to their coupling as described herein) and the membranes 128, 130 (with respect to their orientation in relation to each other as described herein) are adhesive free. As previously noted, this adds to an advantage with respect to limited mess associated with the assembly, disassembly, and use, and makes separation of the membranes simple and efficient.

In addition, because the device 100 comprises two regions, 144, 132 which can be removably coupled to each other, the absorbent membrane 130 can be physically separated (or removed) from the separation membrane 128 by uncoupling the regions 144, 132 from each other. In this way, the flow of plasma can be impeded (e.g., stopped or blocked). Furthermore, the membranes 128, 130 are not in fluid communication with each other when the membranes 128, 130 are not in contact (e.g., side-to-side or overlapping orientation) with each other, but they are in fluid communication when the membranes 128, 130 are in contact with each other. Thus, impeding the flow of plasma can be seen as taking on two configurations (a first orientation where the membranes 128, 130 are in fluid communication and a second orientation where the membranes 128, 130 are not in fluid communication). In the second orientation, the flow of plasma is impeded. In this way, the flow of plasma can be controlled by controlling the fluid communication between the membranes 128, 130 through their orientation with respect to each other (e.g., the first and second orientations described herein).

In some aspects, the separation is permanent. In aspects, the flow of plasma is slowed down (by for example, partially separating the membranes 128, 130 from each other). In aspects, the flow of plasma is blocked by, for example, fully separating or removing the membranes 128, 130 from each other. As herein described, the blocking or stopping (e.g., impeding) the flow of plasma can be irreversible, reversible, permanent or temporary depending on the needs of the user.

Once the plasma collection process is complete (i.e., the plasma has drawn to the absorbent membrane 130 and is therefore collected as the predetermined volume) or the flow of plasma is impeded as described above, the absorbent membrane 130 can be removed, dried and shipped, as required, or the device (as a whole, or as the plasma collection region 144) can be shipped directly to a lab for plasma testing.

It will be understood that any separation membrane 28, 128 and/or absorbent membrane 30, 130 could be used in the devices described herein. In a particular aspect, the membranes are as described in U.S. Pat. Nos. 7,785,865, 8,119, 393, or 7,238,538 or in International Patent Application Publication Nos. WO 2009/143601 or WO 2013/155617, each of which is incorporated herein by reference in its entirety. Typically, the absorbent membrane 30, 130 is of a fixed size which allows for a fixed volume of plasma to be collected. This facilitates the quantitative nature of the devices described herein. It is important to note, however, that the size and shape of the membranes 28, 128, 30, 130 are not limited to those seen in the Figures, and may be modified, so long as the modification permits their use in the devices described herein. This would be understood by one of skill in the art. In addition, because the size of the window 120 can be varied on the device 100, the size of the absorbent membrane 130 can be varied. In this way, the device 100 allows for variation in length of the absorbent membrane 130 and therefore variation in the amount of plasma to be collected.

While the collection units described herein are particularly suited for use in collecting a capillary blood sample, it will be understood that they may find use in collecting any fluid from which solids may be desired to be filtered, such as, for example, a cell suspension, cell culture supernatant, saliva, oral fluid, cerebrospinal fluid, amniotic fluid, milk, colostrum, mammary gland secretion, lymph, urine, sweat, lacrimal fluid, gastric fluid, synovial fluid, mucus, or combinations thereof.

The devices described herein are suitable for use with small volume blood samples, such as less than about 1 ml of blood, from about 1 μl to about 1 ml, from about 1 μl to about 500 μl, from about 1 μl to about 250 μl, from about 1 μl to about 100 μl, from about 1 μl, 5 μl, 10 μl, 15 μl, 20 μl, 25 μl, 30 μl, 35 μl, 40 μl, 45 μl, 50 μl, 60 μl, 70 μl, 80 μl, or 90 μl to about 5 μl, 10 μl, 15 μl, 20 μl, 25 μl, 30 μl, 35 μl, 40 μl, 45 μl, 50 μl, 60 μl, 70 μl, 80 μl, 90 μl, or 100 μl.

The vent 42 has been described as being in the bottom wall of the device. It will be understood that it can instead be in a top wall or a side wall, or a combination of a top, bottom, or side wall. It can also span one or more walls of the device.

It has been explained above that the flow channel typically extends in a downhill manner from the proximal to distal end of the device in the direction of flow of the sample so that gravity can assist in the capillary forces involved in moving the sample along the flow path, however, it will be understood that the flow channel could rather be flat or substantially flat. Thus, it is also contemplated that the blood sample could enter from a lateral side or edge of the separation membrane 28.

Methods of Use

In use, a device 10, 100 described herein is placed near a whole blood sample at the notch 16, so that the blood sample is drawn into the flow channel 26, 126. Once a sufficient volume is collected, the front of the blood sample contacts the separation membrane 28, 128 and is drawn into the separation membrane 28, 128, where the red blood cells are retained, and the plasma continues to travel. In aspects, once the plasma contacts the constriction 34, it will assist in breaking the surface tension and allowing the plasma to enter the chamber 40. The plasma will continue to fill the chamber 40 until the front of the plasma contacts the absorbent membrane 30. In aspects, the orientation of the separation membrane 128 with respect to the absorbent membrane 130, such as, a lateral contact orientation or an overlapping contact orientation, not only allows the membranes 128, 130 to be in fluid communication with each other, but also allows for ease of transfer of the separated plasma from the separation membrane 128 to the absorbent membrane 130. As described herein, the presence of the window 120 in this aspect negates the necessity for the vent 42 of device 10. However, the vent 42 can be included in the device 100 should its functionality be desired.

Once in contact with the absorbent membrane 30 of the first embodiment of the device 10 described herein, the plasma will be drawn in with sufficient force that air will enter the chamber 40 from the vent 42, thereby preventing more plasma from entering the chamber 40 from the separation membrane 28. In this way, the amount of plasma that is collected in the absorbent membrane 30 will correspond to the volume of the chamber 40 and, therefore, there will be a defined and known amount of plasma in the absorbent membrane 30 permitting a quantitative assay on the separated and collected plasma. If a quantitative test is not required, the vent 42 can be omitted.

Once in contact with the absorbent membrane 130 of the second embodiment of the device 100 described herein, in aspects, because the absorbent membrane 130 is of a fixed predetermined size, once the plasma reaches the absorbent membrane 130, the amount of plasma that is collected in the absorbent membrane 130 will correspond to the volume of the absorbent membrane 130, allowing for a quantitative assay on the separated and collected plasma.

In aspects, inclusion of a colorant in the separation membrane 128 and/or the absorbent membrane 30, 130, wherein the colorant becomes mobile in the presence of a fluid and sample and will flow along with the front of the sample and resulting plasma, assists in identifying the plasma front and confirming completion of the plasma collection process. As noted above, once the absorbent membrane 30, 130 is dried, it may be difficult to visualize where the plasma front ceased flowing. The mobilizable colorant remains visible once the absorbent membrane 30, 130 has dried, thereby assisting in quality control and providing a visual indicator of where the absorbent membrane 30, 130 may be cut to still yield a quantitative result, if desired.

Once the plasma is collected in the absorbent membrane 30, 130, the device 10, 100 can be shipped to a lab for further processing. In respect of device 100, this could be the whole device 100, or just the plasma collection region 144 described herein. Alternately the device 10, 100 can be opened and the absorbent membrane 30, 130 may be dried and easily shipped to a central testing facility or tested directly. Likewise, the separation membrane 28, 128 may be shipped separately or together with the absorbent membrane 30, 130 in the case that testing is desired to be carried out on the cellular matter remaining after the plasma has been separated from the whole blood sample.

The above disclosure generally describes the present invention. Changes in form and substitution of equivalents are contemplated as circumstances may suggest or render expedient. Although specific terms have been employed herein, such terms are intended in a descriptive sense and not for purposes of limitation.

All publications, patents, and patent applications cited above are herein incorporated by reference in their entirety to the same extent as if each individual publication, patent or patent application was specifically and individually indicated to be incorporated by reference in its entirety.

Although preferred aspects of the invention have been described herein in detail, it will be understood by those skilled in the art that variations may be made thereto without departing from the spirit of the invention or the scope of the appended claims.

The invention claimed is:

1. A device for collecting plasma from a blood sample, the device comprising a body defining a flow channel extending laterally between a proximal and a distal end of the device, the flow channel comprising:
   a membrane region comprising a separation membrane for filtering red blood cells from the plasma;
   a plasma collection region comprising an absorbent membrane for collecting the plasma; and
   a flow path region upstream of the membrane region; and
   a chamber for separating the membrane region from the plasma collection region;
   wherein flow of the plasma from the separation membrane to the absorbent membrane is impedable; and
   wherein the separation membrane and the absorbent membrane do not touch one another.

2. The device of claim 1, wherein the flow of the plasma is blocked by separating the membrane region from the plasma collection region.

3. The device of claim 1, wherein the plasma collection region and the membrane region are removably couplable.

4. The device of claim 3, wherein the membrane region and/or the plasma collection region comprises a tongue that engages with the plasma collection region and/or the membrane region.

5. The device of claim 4, wherein the tongue comprises a protrusion that engages with a corresponding void.

6. The device of claim 1, wherein the plasma collection region comprises a top portion and a bottom portion that are removably couplable and wherein the membrane region comprises a top portion and a bottom portion that are removably couplable.

7. The device of claim 6, wherein the bottom portion of the plasma collection region comprises a stand member for inclining the device on a surface.

8. The device of claim 1, wherein the plasma collection region and the membrane region are removably couplable without an adhesive.

9. The device of claim 1, wherein the absorbent membrane is of a predefined volume of from about 5 µl to about 50 µl, about 5 µl to about 25 µl, about 10 µl to about 20 µl, or about 10 µl to about 15 µl.

10. The device of claim 1, wherein the membrane region is enlarged such that a top and bottom wall of the flow channel in the membrane region does not contact the separation membrane.

11. The device of claim 10, wherein the membrane region comprises one or more supports that extend from a top and/or bottom wall of the flow channel for supporting the separation membrane.

12. The device of claim 1, wherein the device is configured for easy removal of the absorbent membrane.

13. The device of claim 1, wherein the device further comprises a handle at the distal end.

14. The device of claim 1, wherein the separation membrane has a pore size that accommodates red blood cells without substantial hemolysis, wherein the separation membrane has an average pore size of from about 6 µm to about 8 µm.

15. The device of claim 1, wherein the separation membrane and/or the absorbent membrane comprises a colorant that mobilizes with a front of the plasma.

16. The device of claim 1, wherein the device allows for collection and flow of the blood from the proximal end through the separation membrane, wherein the red blood cells are retained, and the plasma continues to flow into the absorbent membrane in a single step.

17. The device of claim 1, wherein the device does not require the addition of a buffer or diluent to effect flow of the blood through the flow channel.

18. The device of claim 1, further comprising a window for visually inspecting the sample, for air drying the sample and/or for separating the separation membrane and the absorbent membrane to impede the flow of plasma.

19. The device of claim 1, wherein the blood sample does not require an anti-coagulant.

20. A one-step method of collecting a plasma sample from a blood sample, the method comprising administering the blood sample to the device of claim 1 and allowing the sample to be drawn into and through the flow channel.

21. The device of claim 1, wherein the flow path region upstream of the membrane region is membrane-free.

* * * * *